United States Patent
Albert et al.

(10) Patent No.: US 6,846,814 B2
(45) Date of Patent: Jan. 25, 2005

(54) NEUROKININ ANTAGONISTS FOR USE AS MEDICAMENTS

(75) Inventors: Jeffrey Scott Albert, Wilmington, DE (US); Peter Bernstein, Wilmington, DE (US); Cyrus Ohnmacht, Jr., Wilmington, DE (US); Keith Russell, Wilmington, DE (US); Ashokkumar Bhikkappa Shenvi, Wilmington, DE (US)

(73) Assignee: Astra Zeneca AB, Sodertalje (SE)

( * ) Notice: Subject to any disclaimer, the term of this patent is extended or adjusted under 35 U.S.C. 154(b) by 69 days.

(21) Appl. No.: 10/240,852
(22) PCT Filed: Apr. 5, 2001
(86) PCT No.: PCT/SE01/00754
§ 371 (c)(1),
(2), (4) Date: Oct. 2, 2002
(87) PCT Pub. No.: WO01/77089
PCT Pub. Date: Oct. 18, 2001

(65) Prior Publication Data
US 2003/0158170 A1 Aug. 21, 2003

Related U.S. Application Data
(60) Provisional application No. 60/195,177, filed on Apr. 6, 2000, and provisional application No. 60/195,365, filed on Apr. 6, 2000.

(51) Int. Cl.⁷ .................. C07D 417/06; C07D 403/06; A61K 31/395; A61K 31/554; A61P 25/24

(52) U.S. Cl. ............ 514/183; 514/211.04; 514/211.11; 540/455; 540/461; 540/488; 540/522

(58) Field of Search ................. 540/455, 461, 540/488, 522; 514/183, 211, 211.11

(56) References Cited

FOREIGN PATENT DOCUMENTS

| | | |
|---|---|---|
| WO | WO 9628158 A1 | 9/1996 |
| WO | WO 0002859 A1 | 1/2000 |
| WO | WO 0020003 A1 | 4/2000 |
| WO | WO 0020389 A1 | 4/2000 |
| WO | WO 0034243 A1 | 6/2000 |
| WO | WO 0064423 A2 | 11/2000 |

OTHER PUBLICATIONS

Swain, C. et al, Ann. Reports Med. Chem., vol. 34, 1999, pp. 51–60.*
Asianian R. et al, Ann. Reports Med. Chem., vol. 36, 2001, pp. 31–40.*
* cited by examiner Primary Examiner—Thomas C. McKenzie
(74) Attorney, Agent, or Firm—Kenneth F. Mitchell

(57) ABSTRACT

Compounds having the general formula

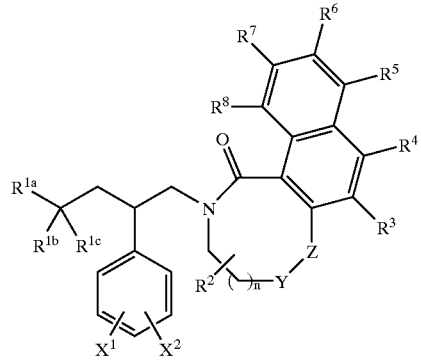

wherein $R^{1a}$, $R^{1b}$, $R^{1c}$, $R^2$, $R^3$, $R^4$, $R^5$, $R^6$, $R^7$, $R^8$, $X^1$, $X^2$, Y, Z and n are as defined in the specification, methods of using such compounds for the treatment of diseases and pharmaceutical composition comprising such compounds.

15 Claims, No Drawings

NEUROKININ ANTAGONISTS FOR USE AS MEDICAMENTS

This is a §371 application of PCT Application PCT/SE01/00754, filed Apr. 5, 2001, pending, which claims the priority of U.S. Provisional Applications No. 60/195,177 and 60/ 195,365, both filed Apr. 6, 2000.

BACKGROUND

The mammalian neurokinins comprise a class of peptide neurotransmitters which are found in the peripheral and central nervous systems. The three principal neurokinins are Substance P (SP), Neurokinin A (NKA) and Neurokinin B (NKB).

There are also N-terminally extended forms of at least NKA. At least three receptor types are known for the three principal neurokinins. Based upon their relative selectivities favoring the neurokinin agonists SP, NKA and NKB, the receptors are classified as neurokinin 1 ($NK_1$), neurokinin 2 ($NK_2$) and neurokinin 3 ($NK_3$) receptors, respectively.

It is now recognized that anxiety, stress, and depression are interrelated conditions (File S E *Pharmacol, Biochem & Behavior* 54/1:3–12, 1996). Moreover, these complex emotional states cannot be due simply to defects in a single neurotransmitter although 5-HT has been ascribed a principal role (Graeff et al., *Pharmacol, Biochem & Behavior* 54/1: 129–141, 1996). Substance P (SP) was one of the first neuropeptides to be identified in mammalian brain and it is now accepted that all three tachykinins are found within the CNS (Iversen L L *J Psychopharmacol* 3/1: 1–6, 1989), particularly in the striatonigral neurons, hypothalamus and limbic forebrain (ibid). $NK_1$ and $NK_3$ receptors have been identified in the brain as well (Beaujouan et al., *Neurosci.* 18: 857–875, 1986). Controversy has existed regarding the presence of the $NK_2$ receptor in brain, although recent evidence shows receptor localization in at least the septal region (Steinberg et al., *Eur J Neurosci* 10/7:2337–45 1998).

Pharmacological evidence supporting a role for either $NK_1$ or $NK_2$ receptors in anxiety disorders has been accumulating from assorted animal behavioral tests (for examples, see Table 1). Animal models of depression, however, have been used rarely to define the potential utility of NK receptor antagonists. SP stimulates the turnover of other neurotransmitters involved in depression, i.e., 5-HT in the raphe nucleus, an area thought to be linked to depressive phenomena (Forchetti et al., *J. Neurochem.* 38: 1336–1341, 1982). When injected centrally to nuclei responsible for control of emotion and stress, SP evokes a hemodynamic pressor response bridging this peptide to stress induced hypertension (Ku et al., *Peptides;* 1914:677–82, 1998). Moreover, rises in both heart rate and mean arterial blood pressure evoked by physical stress can be blocked in rodents by centrally administered $NK_1$ receptor antagonists (Culman et al., *J Pharmacol Exp Ther* 280/1:238–46, 1997).

TABLE 1

Neurokinin receptor antagonist activity in behavioral tests of anxiety/depression.

| Author | Cpd (Receptor type) | Behavioral Test | Outcome |
|---|---|---|---|
| Teixeira et al., Eur J Pharmacol 5;311(1):7–14, 1996. | $NK_1$ agonists & FK888 ($NK_1$) SR48968 ($NK_2$) | Elevated plus-maze | agonists-anxiogenic antagonists-anxiolytic |
| File Pharm Bio B 58(3):747–752, 1997. | CGP 49823 ($NK_1$) | Social interaction | anxiolytic |
| Vassout et al Neuropeptides 26/S1:38, 1994. | CGP 49823 ($NK_1$) | Social interaction test Elevated plus-maze Forced swim test (depression model) | anxiolytic inactive antidepressant (only at 30 mg/kg bid) |
| Stratton et al., Eur. J. Pharmacol. 250: R11–12, 1993. | GR100679 ($NK_2$) SR48968 ($NK_2$) | Light-dark box | anxiolytic |
| Walsh et al., Psychopharmacology 121: 186–191, 1995. | GR159897 ($NK_2$) SR48968 ($NK_2$) | Light-dark box Marmoset human intruder | anxiolytic anxiolytic |

DESCRIPTION

This invention relates to internally cyclized naphthamide compounds; to pharmaceutical compositions containing such compounds; as well as to their uses and processes for their preparation. These compounds antagonize the pharmacological actions of the neurokinin 1 ($NK_1$) receptor. These compounds are useful whenever such antagonism is desired. Thus, such compounds are of value in the treatment of those diseases in which Substance P is implicated, for example, in the treatment of major depressive disorder, severe anxiety disorders, stress disorders, major depressive disorder with anxiety, eating disorders, bipolar disorder, substance use disorder, schizophrenic disorders, psychotic disorders, movement disorders, cognitive disorders, depression and/or anxiety, mania or hypomania, aggressive behaviour, obesity, emesis, rheumatoid arthritis, Alzheimer's disease, cancer, oedema, allergic rhinitis, inflammation, pain, gastrointestinal-hypermotility, Huntington's disease, chronic obstructive pulmonary disorder (COPD), hypertension, migraine, bladder hypermotility, or urticaria.

Accordingly, the present invention provides the compounds of the general formula Ia:

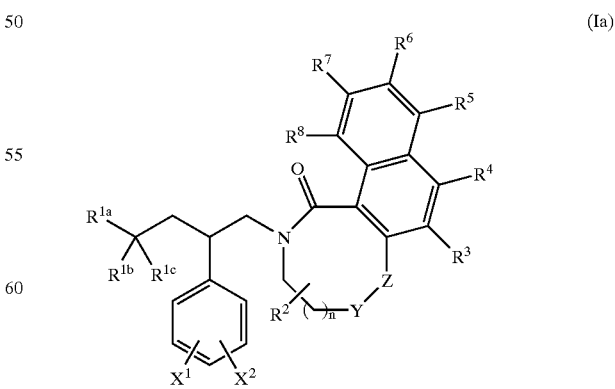

The compounds of the present invention may possess a number of chiral centres, for example at —CH(Ph—$^1$, $X^2$)—, and at —CH($R^2$)—. The present invention covers all isomers, diastereoisomers and mixtures thereof that antagonize $NK_1$.

The preferred configuration at —CH(Ph—$X^1,X^2$)— is shown in formula (Ib) hereinbelow:

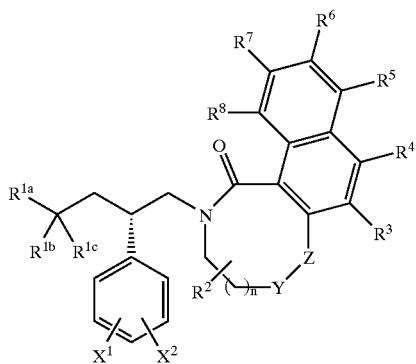

(Ib)

$X^1$ and $X^2$ are independently hydrogen or halo, provided that at least one of $X^1$ or $X^2$ is halo. Favourably, $X^1$ and $X^2$ are both chloro. In a preferred aspect Ph-$^1,X^2$ is 3,4-dichlorophenyl.

$R^{1a}$ is H, $NR^9R^{10}$, —$OR^{10}$, Cl, Br,

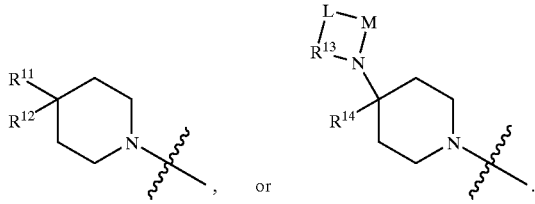

In another embodiment, $R^{1a}$ is H, $NR^9R^{10}$, —$OR^9$,

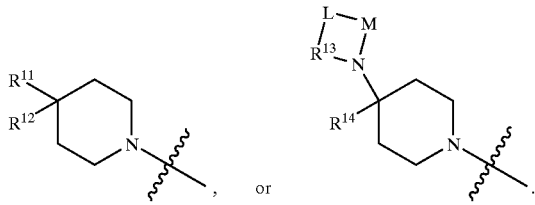

$R^{1b}$ and $R^{1c}$ are independently H or —$OR^9$, or $R^{1b}$ and $R^{1c}$ together are =O, =$CH_2$ or —$OCH_2CH_2O$—.

In one embodiment, $R^{1a}$ is H, $NR^9R^{10}$ or —$OR^9$. In another embodiment, $R^{1a}$ is

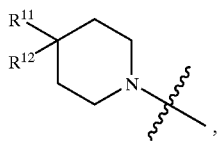

$R^{1b}$ is H and $R^{1c}$ is H. And in another embodiment, $R^{1a}$ is

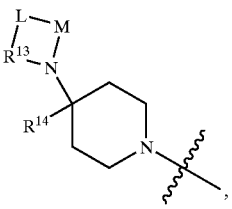

$R^{1b}$ is H and $R^{1c}$ is H.

In another embodiment, $R^{1a}$ is H, $NR^9R^{10}$, —$OR^{10}$, Cl or Br; and $R^{1b}$ and $R^{1c}$ are independently H or —$OR^9$, or $R^{1b}$ and $R^{1c}$ together are =O, =$CH_2$ or —$OCH_2CH_2O$—.

In another embodiment, $R^{1a}$ is Cl or Br; and $R^{1b}$ and $R^{1c}$ are both H.

In another embodiment, $R^{1a}$ is $NR^9R^{10}$, —$OR^{10}$; and $R^{1b}$ and $R^{1c}$ are both H or $R^{1b}$ and $R^{1c}$ together are =O.

$R^2$ is H, oxo, —$OR^9$ or —$CH_3$. In one embodiment, $R^2$ is —$OR^5$ or —$CH_3$.

$R^3$, $R^4$, $R^5$, $R^6$, $R^7$ and $R^8$ are each independently selected from H, cyano, nitro, trifluoromethoxy, trifluoromethyl, $C_{1-6}$alkylsulfonyl, halo, —$OR^9$, —$OCH_2O$—, $C_{1-6}$alkyl, $C_{2-6}$alkenyl, $C_{2-6}$alkynyl, —C(=O)$OR^9$, —C(=O)$NR^9R^{10}$, —OC(=O)$R^9$, —$NR^9C$(=O)$R^{10}$, aminosulfonyl and $C_{1-6}$alkyl substituted by any of the hereinabove substituents; wherein at least two of $R^3$, $R^4$, $R^5$, $R^6$, $R^7$ and $R^8$ are H. In another embodiment, $R^5$, $R^6$, $R^7$ and $R^8$ are each H.

In one embodiment, $R^3$, $R^4$, $R^5$, $R^6$, $R^7$ and $R^8$ are selected from H, cyano, nitro, —S(=O)$C_{1-6}$alkyl, halo, —$OR^9$, —$OCH_2O$—, $C_{1-6}$alkyl, $C_{2-6}$alkenyl, $C_{2-6}$alkynyl, —C(=O)$OR^9$, —C(=O)$NR^9R^{10}$, —OC(=O)$R^9$, —$NR^9C$(=O)$R^{10}$, aminosulfonyl and —$C_{1-6}$alkylcyano; wherein at least three of $R^3$, $R^4$, $R^5$, $R^6$, $R^7$ and $R^8$ are H.

In another embodiment, $R^3$, $R^4$, $R^5$, $R^6$, $R^7$ and $R^8$ are selected from H, cyano, methoxy, ethoxy, isopropoxy, fluoro, bromo, chloro, iodo, nitro, cyanomethyl, carboxy, carbamoyl, ethynyl, methyl, ethyl, dimethylcarbamoyl, methylsulfonyl, aminosulfonyl, prop-2-enyl, acetyl and acetylamino; wherein at least five of $R^3$, $R^4$, $R^5$, $R^6$, $R^7$ and $R^8$ are H.

In another embodiment, $R^3$, $R^4$, $R^5$, $R^6$, $R^7$ and $R^8$ are selected from H, cyano, methoxy, ethyl, fluoro and nitro; wherein at least three of $R^3$, $R^4$, $R^5$, $R^6$, $R^7$ and $R^8$ are H.

$R^9$ is independently selected from H, $C_{1-6}$alkyl, $C_{1-4}$alkoxy, and —$OCH_2(CH_2)_n$phenyl.

$R^{10}$ is independently H or $C_{1-6}$alkyl, hydroxy$C_{1-6}$alkyl, ($NR^9R^9$)$C_{1-6}$alkyl, ($NR^9R^9$)C(=O)$C_{1-6}$alkyl, —$(CH_2)_oR^{15}$.

In another embodiment, $R^9$ and $R^{10}$ are each independently H or $C_{1-6}$alkyl;

$R^{11}$ is phenyl, substituted in at least the ortho position by $C_{1-6}$alkylthio, $C_{1-6}$alkylsulfinyl, $C_{1-6}$alkylsulfonyl, trifluoromethylthio, trifluoromethylsulfinyl, $C_{1-6}$alkanesulfonamido, $C_{1-6}$alkanoyl, $C_{1-6}$alkoxy-carbonyl, succinamido, carbamoyl, $C_{1-6}$alkylcarbamoyl, di-$C_{1-6}$alkylcarbamoyl, $C_{1-6}$alkoxy-$C_{1-6}$alkylcarbamoyl, N-methylcarbamoyl, $C_{1-6}$alkanoylamino, ureido, $C_{1-6}$ureido, di-$C_{1-6}$alkylureido, amino, $C_{1-6}$alkylamino, or di-$C_{1-6}$alkylamino.

$R^{12}$ is selected from hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl and bis($C_{1-6}$alkyl)carbamoyl.

$R^{13}$ is —$CH_2CH_2$—, —$CH_2CH_2CH_2$— or —$CH_2CH_2CH_2CH_2$—.

$R^{14}$ is hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl or di-$C_{1-6}$alkylcarbamoyl.

$R^{15}$ is a 5- or 6-membered saturated or unsaturated heterocycle containing 1 or 2 heteroatoms selected from nitrogen, oxygen and sulfur and additionally subsituted with 0 or 1 oxo groups; or $R^{15}$ is phenyl substituted by 0, 1, or 2 substitutents selected from halogen, $C_{1-4}$alkoxy, vicinal-methylenedioxy, $-S(=O)_nC_{1-4}$alkyl, $-S(=O)_2NH_2$ and $C_{1-4}$alkyl;

M is $-C(=O)-$ or $-S(=O)_2-$.

L is $-NH-$ or $-CH_2-$.

Y and Z are independently selected from $CH_2$, O, S, S=O and $S(=O)_2$, wherein at least one of Y and Z is $CH_2$. In another embodiment, Y and Z are $CH_2$ or O, wherein Y does not equal Z.

n is independently, at each instance, 0 or 1;

o is independently, at each instance, 1, 2 or 3.

Another aspect of the invention involves a pharmaceutical composition comprising a therapeutically effective amound of a compound of formula Ia.

Another aspect of the invention involves a method of treating major depressive disorder, severe anxiety disorders, stress disorders, major depressive disorder with anxiety, eating disorders, bipolar disorder, general and specific craving, substance use disorder, schizophrenic disorders, psychotic disorders, movement disorders, cognitive disorders, depression and/or anxiety, mania or hypomania, aggressive behaviour, obesity, emesis, rheumatoid arthritis, Alzheimer's disease, cancer, oedema, allergic rhinitis, inflammation, pain, gastrointestinal-hypermotility, Huntington's disease, COPD, hypertension, migraine, bladder hypermotility, or urticaria comprising administering an effective amount of an NK1 antagonist of formula Ia.

Particular compounds of this invention are provided as the Examples hereinbelow.

$C_{Y-Z}$alkyl, unless otherwise specified, means an alkyl chain containing a minimum Y total carbon atoms and a maximum Z total carbon atoms. These alkyl chains may be branched or unbranched, cyclic, acyclic or a combination of cyclic and acyclic. For example, the following substituents would be included in the general description "$C_{4-7}$alkyl":

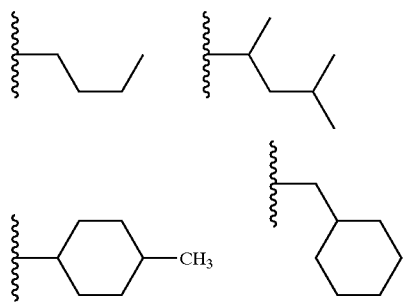

Pharmaceutically-acceptable salts may be prepared from the corresponding acid in conventional manner. Non-pharmaceutically-acceptable salts may be useful as intermediates and as such are another aspect of the present invention.

The symbol "=O" means a double bonded oxygen, and when this symbol is used attached to a carbon it forms a carbonyl group.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans so that, for example, a daily dose of 0.01 to 25 mg/kg body weight (and preferably of 0.1 to 5 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt thereof may be used.

Therefore in a further aspect, the present invention provides a compound of the formula (I) or a pharmaceutically acceptable salt thereof for use in a method of therapeutic treatment of the human or animal body.

In yet a further aspect the present invention provides a method of treating a disease condition wherein antagonism of the $NK_1$ receptor is beneficial which comprises administering to a warm-blooded animal an effective amount of a compound of the formula (I) or a pharmaceutically-acceptable salt thereof. The present invention also provides the use of a compound of the formula (I) or a pharmaceutically acceptable salt thereof in the preparation of a medicament for use in a disease condition wherein antagonism of the $NK_1$ receptor is beneficial.

The compounds of the formula (I) and their pharmaceutically acceptable salts may be made by processes as described and exemplified herein and by processes similar thereto and by processes known in the chemical art. If not commercially available, starting materials for these processes may be made by procedures which are selected from the chemical art using techniques which are similar or analogous to the synthesis of known compounds.

It is well known in the art how to prepare optically-active forms (for example, by resolution of the racemic form or by synthesis from optically-active starting materials) and how to determine the $NK_1$ antagonist properties by the standard tests known in the art and those described hereinafter.

Some individual compounds within the scope of this invention may contain double bonds. Representations of double bonds in this invention are meant to include both the E and the Z isomer of the double bond. Additionally, some species within the scope of this invention may contain one or more asymmetric centers. This invention includes the use of any of the optically pure stereoisomers as well as any combination of stereoisomers.

In general, the macrocyclic naphthamides can exist as a mixture of conformational isomers (atropisomers) ("The Chemistry of Rotational Isomers"; Oki, M.; Springer Verlag, NY; 1993). Where individual atropisomers have been isolatable, distinct chemical and biological properties have been observed. The compounds of this invention comprise both mixtures of, and individual, atropisomers.

The following biological test methods, data and Examples serve to illustrate and further describe the invention.

The utility of a compound of the invention or a pharmaceutically acceptable salt thereof (hereinafter, collectively referred to as a "compound") may be demonstrated by standard tests and clinical studies, including those disclosed in the publications described below.

SP Receptor Binding Assay (Test A)

The ability of a compound of the invention to antagonize the binding of SP at the $NK_1$ receptor may be demonstrated using an assay using the human $NK_1$ receptor expressed in Mouse Erythroleukemia (MEL) cells. The human $NK_1$ receptor was isolated and characterized as described in: B. Hopkins, et al. "Isolation and characterization of the human lung $NK_1$ receptor cDNA" *Biochem. Biophys. Res. Comm.*, 1991, 180, 1110–1117; and the $NK_1$ receptor was expressed in Mouse Erythroleukemia (MEL) cells using a procedure similar to that described in Test B below.

Neurokinin A (NKA) Receptor Binding Assay (Test B)

The ability of a compound of the invention to antagonize the binding of NKA at the $NK_2$ receptor may be demonstrated using an assay using the human $NK_2$ receptor expressed in Mouse Erythroleukemia (MEL) cells, as described in: Aharony, D., et al. "Isolation and Pharmacological Characterization of a Hampster Neurokinin A Receptor cDNA" *Molecular Pharmacology*, 1994, 45, 9–19.

The selectivity of a compound for binding at the $NK_1$ and the $NK_2$ receptors may be shown by determining its binding at other receptors using standard assays, for example, one using a tritiated derivative of NKB in a tissue preparation selective for $NK_3$ receptors. In general, the compounds of the invention which were tested demonstrated statistically significant binding activity in Test A and Test B with a $K_i$ of 1 mM or much less typically being measured.

Rabbit Pulmonary Artery: $NK_1$ in vitro Functional Assay (Test C)

The ability of a compound of the invention to antagonize the action of the agonist Ac-[$Arg^6$, $Sar^9$, $Met(O_2)^{11}$] Substance P (6–11), ASMSP, in a pulmonary tissue may be demonstrated as follows.

Male New Zealand white rabbits are euthanized via i.v. injection into the ear vein with 60 mg/kg Nembutal (50 mg/mL). Preceding the Nembutal into the vein is Heparin (1000 units/mL) at 0.0025 mL/kg for anticoagulant purposes. The chest cavity is opened from the top of the rib cage to the sternum and the heart, lungs and part of the trachea are removed. The pulmonary arteries are isolated from the rest of the tissues and cut in half to serve as pairs.

The segments are suspended between stainless steel stirrups, so as not to remove any of the endothelium, and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; indomethacin, 0.005 (to inhibit cyclooxygenase); and dl-Propranolol, 0.001 (to block β receptors); gassed continuously with 95% $O_2$-5% $CO_2$. Responses are measured on a Grass polygraph via Grass FT-03 transducers.

Initial tension placed on each tissue is 2 grams, which is maintained throughout the 1.0 hour equilibration period. Tissues are washed with the physiological salt solution at 15 minute intervals. At the 30 and 45 minute wash the following treatments are added: $1×10^{-6}$ M Thiorphan (to block E.C.3.4.24.11), $3×10^{-8}$ M (S)-N-[2-(3,4-dichlorophenyl)-4-[4-(2-oxoperhydropyrimidin-1-yl)piperidino]butyl]-N-methylbenzamide (to block $NK_2$ receptors), and the given concentration of the compound being tested. At the end of the 1.0 h equilibration, $3×10^{-6}$ M phenylephrine hydrochloride is added for 1.0 h. At the end of 1.0 h, a dose relaxation curve to ASMSP is done. Each tissue is treated as a individual and is considered finished when it fails to relax further for 2 consecutive doses. When a tissue is complete, $1×10^{-3}$ M Papaverine is added for maximum relaxation.

Percent inhibition is determined when a tested compound produces a statistically significant ($p<0.05$) reduction of the total relaxation which is calculated using the total relaxation of the Papaverine as 100%. Potencies of the compounds are determined by calculating the apparent dissociation constants ($K_B$) for each concentration tested using the standard equation:

$$K_B = [\text{antagonist}]/(\text{dose ratio} - 1)$$

where dose ratio=antilog[(agonist −log molar $EC_{50}$ without compound)−(−log molar $EC_{50}$ with compound)]. The $K_B$ values may be converted to the negative logarithms and expressed as −log molar $K_B$ (i.e. $pK_B$). For this evaluation, complete concentration-response curves for agonist obtained in the absence and presence of the compound tested using paired pulmonary artery rings. The potency of the agonist is determined at 50% of its own maximum relaxation in each curve. The $EC_{50}$ values are converted to negative logarithms and expressed as −log molar $EC_{50}$.

NK$_2$ in Vitro Functional Assay (Test D)

The ability of a compound of the invention to antagonize the action of the agonist [β-ala8] NKA (4-10), BANK, in a pulmonary tissue may be demonstrated as follows. Male New Zealand white rabbits are euthanized via i.v. injection into the ear vein with 60 mg/kg Nembutal (50 mg/mL). Preceding the Nembutal into the vein is Heparin (1000 units/mL) at 0.0025 mL/kg for anticoagulant purposes. The chest cavity is opened from the top of the rib cage to the sternum and a small incision is made into the heart so that the left and right pulmonary arteries can be cannulated with polyethylene tubing (PE260 and PE190 respectively). The pulmonary arteries are isolated from the rest of the tissues, then rubbed over an intimal surface to remove the endothelium, and cut in half to serve as pairs. The segments are suspended between stainless steel stirrups and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; and indomethacin, 0.005 (to inhibit cyclooxygenase); gassed continuously with 95% $O_2$-5% $CO_2$. Responses are measured on a Grass polygraph via Grass FT-03 transducers.

Initial tension placed on each tissue is 2 g, which is maintained throughout the 45 min equilibration period. Tissues are washed with the physiological salt solution at 15 min intervals. After the 45 min equilibration period, $3 \times 10^{-2}$ M KCl is given for 60 min to test the viability of the tissues. The tissues are then washed extensively for 30 min. The concentration of the compound being tested is then added for 30 min. At the end of the 30 min, a cumulative dose response curve to BANK is performed. Each tissue is treated as a individual and is considered finished when it fails to contract further for 2 consecutive doses. When a tissue is complete, $3 \times 10^{-2}$ M $BaCl_2$ is added for maximum contraction.

Percent inhibition is determined when a tested compound produces a statistically significant (p<0.05) reduction of the total contraction which is calculated using the total contraction of the $BaCl_2$ as 100%. Potencies of the compounds are determined by calculating the apparent dissociation constants ($K_B$) for each concentration tested using the standard equation:

$$K_B = [\text{antagonist}]/(\text{dose ratio} - 1)$$

where dose ratio=antilog[(agonist −log molar $EC_{50}$ without compound)−(−log molar $EC_{50}$ with compound)]. The $K_B$ values may be converted to the negative logarithms and expressed as −log molar $K_B$ (i.e. $pK_B$). For this evaluation, complete concentration-response curves for agonist obtained in the absence and presence of the compound tested using paired pulmonary artery rings. The potency of the agonist is determined at 50% of its own maximum relaxation in each curve. The $EC_{50}$ values are converted to negative logarithms and expressed as −log molar $EC_{50}$.

NK$_1$ and NK$_2$ in Vivo Functional Assay (Test E)

The activity of a compound as an antagonist of NK$_1$ and/or NK$_2$ receptors also may be demonstrated in vivo in laboratory animals as described in: Buckner et al. "Differential Blockade by Tachykinin NK$_1$ and NK$_2$ Receptor Antagonists of Bronchoconstriction Induced by Direct-Acting Agonists and the Indirect-Acting Mimetics Capsaicin, Serotonin and 2-Methyl-Serotonin in the Anesthetized Guinea Pig." *J. Pharm. Exp. Ther.*, 1993, Vol 267(3), pp.1168–1175. The assay is carried out as follows.

Compounds are tested in anesthetized guinea pigs pretreated with i.v. indomethacin (10 mg/kg, 20 min), propranolol (0.5 mg/kg, 15 min), and thiorphan (10 mg/kg, 10 min).

Antagonists or vehicle are administered i.v. and orally, 30 and 120 min prior to increasing concentrations of agonist, respectively. The agonists used in these studies are ASMSP (Ac-[$Arg^6$,$Sar^9$,$Met(O_2)^{11}$]-SP(6–11)) and BANK (β-ala-8 NKA4–10).

Administered i.v., ASMSP is selective for NK$_1$ receptors, and BANK is selective for NK$_2$ receptors. Maximum response is defined as zero conductance ($G_L$, 1/Rp). $ED_{50}$ values are calculated (the dose of agonist resulting in a reduction of $G_L$ to 50% of baseline), and converted to the negative logarithm ($-\log ED_{50}$). The $ED_{50}$ values, obtained in the presence (P) and absence (A) of antagonist, are used to calculate a Dose Ratio (P/A), an expression of potency. Data are expressed as mean ± SEM and statistical differences were determined using ANOVA/Tukey-Kramer and Student's t-test, with p<0.05 considered statistically significant.

Compounds of the present invention exhibit marked activity in the foregoing tests and are considered useful for the treatment of those diseases in which the NK$_1$ and/or NK$_2$ receptor is implicated, for example, in the treatment of asthma and related conditions.

EXAMPLES

The invention will now be illustrated by the following non-limiting examples, in which, unless stated otherwise:

(i) temperatures are given in degrees Celsius (° C.); unless otherwise stated, operations were carried out at room or ambient temperature, that is, at a temperature in the range of 18–25° C.;

(ii) organic solutions were dried over anhydrous sodium sulfate; evaporation of solvent was carried out using a rotary evaporator under reduced pressure (600–4000 Pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition;

(vi) final products had satisfactory proton nuclear magnetic resonance (NMR) spectra;

(vii) when given, NMR data is in the form of delta values for major diagnostic protons, given in parts per million (ppm) relative to tetramethylsilane (TMS) as an internal standard, determined at 300 MHz using deuterated chloroform (CDCl₃) as solvent; conventional abbreviations for signal shape are used; for AB spectra the directly observed shifts are reported; coupling constants (J) are given in Hz; Ar designates an aromatic proton when such an assignment is made;

(viii) reduced pressures are given as absolute pressures in pascals (Pa); elevated pressures are given as gauge pressures in bars;

(ix) solvent ratios are given in volume:volume (v/v) terms; and (x) Mass spectra (MS) were run using an automated system with atmospheric pressure chemical ionization (APCI). Generally, only spectra where parent masses are observed are reported. The lowest mass major ion is reported for molecules where isotope splitting results in multiple mass spectral peaks (for example when chlorine is present).

Terms and abbreviations: solvent mixture compositions are given as volume percentages or volume ratios. In cases where the NMR spectra are complex, only diagnostic signals are reported. AcOH=acetic acid, atm=atmospheric pressure, Boc=t-butoxycarbonyl, Cbz=benzyloxycarbonyl, DCM=methylene chloride, DIPEA=diisopropylethylamine, DMF=N,N-dimethylformamide, DMSO=dimethyl sulfoxide, Et₂O=diethyl ether, EtOAc=ethyl acetate, equiv.=equivalent(s), h=hour(s), HPLC=high performance liquid chromatography, MeOH=methanol, min=minutes, NMR=nuclear magnetic resonance, RT=room temperature, psi=pounds per square inch, TFA=trifluoroacetic acid, THF=tetrahydrofuran.

Where noted that a compound was converted to the citrate salt, the free base was combined with citric acid (1.0 equivalents) in methanol, concentrated under reduced pressure and dried under vacuum (25–70° C.).

Example 1

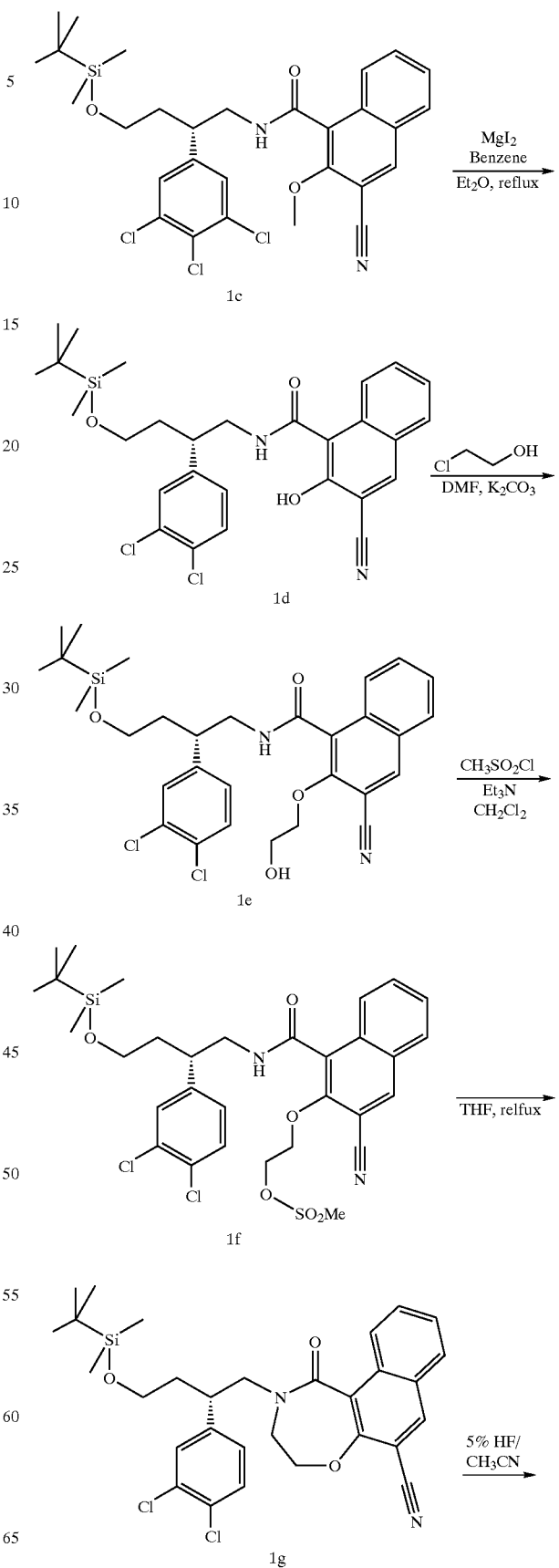

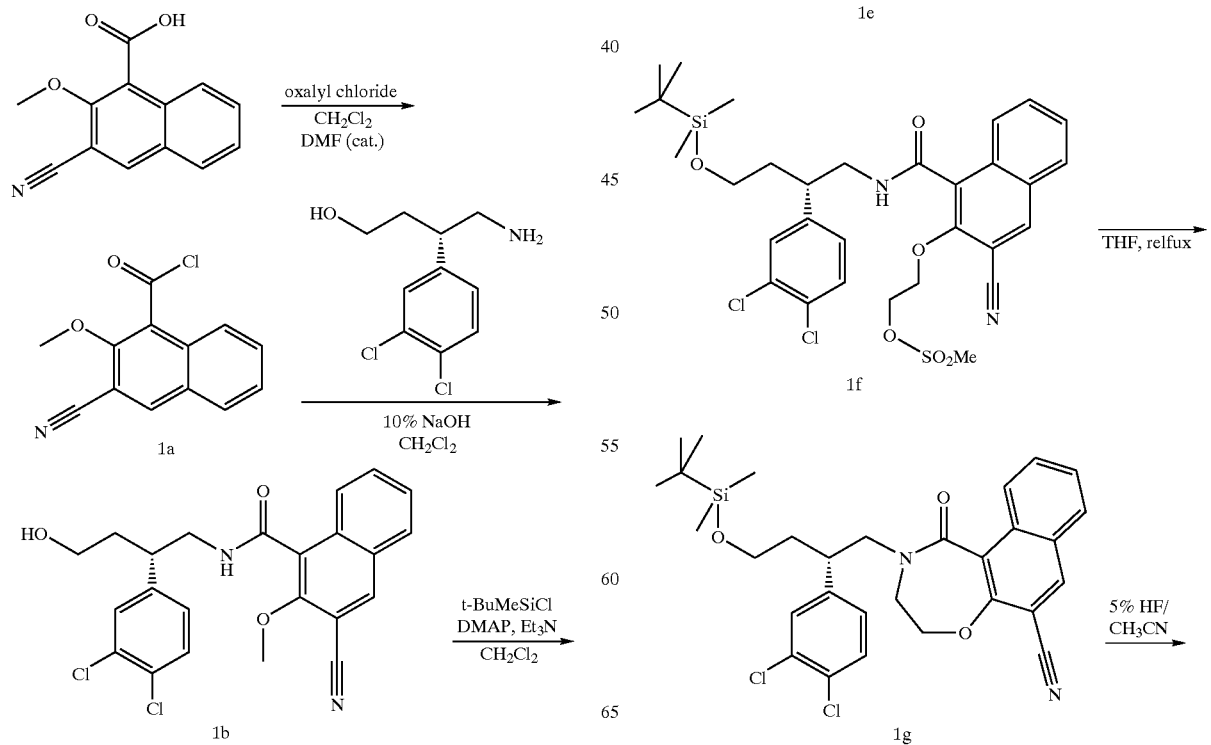

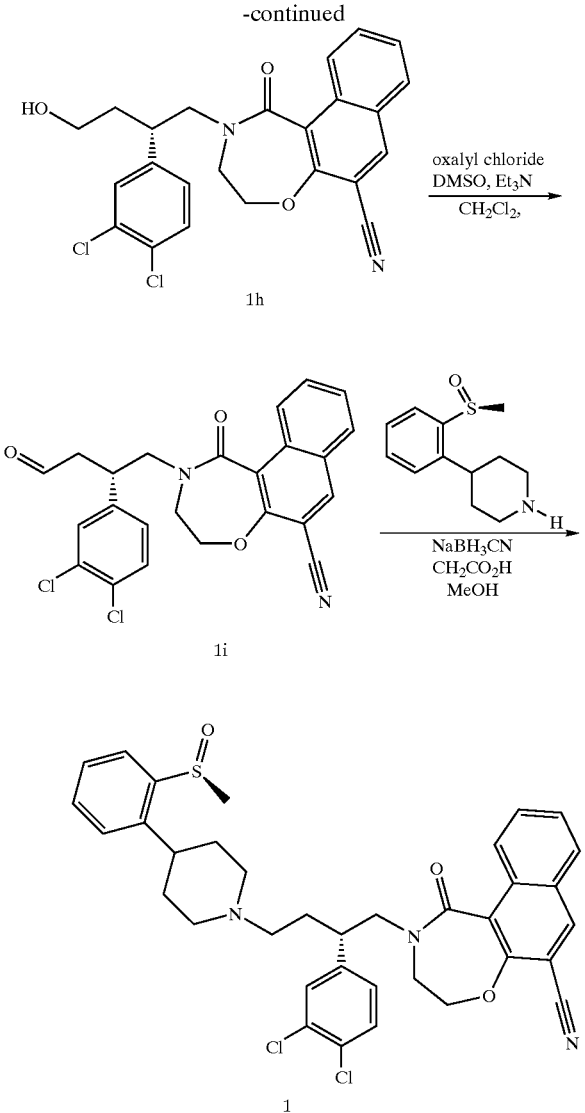

To a stirred solution of 4-[(S)-2-methylsulfinylphenyl]-piperidine (0.078 g, 0.326 mmol) and MeOH (8 mL) was added AcOH (0.02 mL, 0.359 mmol), a solution of 1i (0.148 g, 0.326 mmol) in MeOH (6 mL). The mixture was stirred at RT for 30 min and a solution of sodium cyanoborohydride (0.023 g, 0.359 mmol) in MeOH (2 mL) was added and stirring continued at RT overnight. The mixture was quenched with saturated NaHCO$_3$ and partitioned between DCM and water. The organic phase was collected, consecutively washed with saturated aqueous NaHCO$_3$ and water, dried (Na$_2$SO$_4$), filtered and the solvent removed in vacuo. The crude product was purified by gradient chromatography (2%, 5% MeOH/DCM) to yield 1 (0.194 g, 90%) as a white solid which was converted to the citrate salt. $^1$H NMR (300 MHz, CDCl$_3$) δ 8.25 (s, 1H), 8.0 (m, 2H), 7.84 (d, 1H), 7.66 (t, 1H), 7.56 (t, 1H), 7.48–7.35 (m, 5H), 7.17 (dd, 1H), 4.43–4.30 (m, 2H), 4.4 (m, 1H), 3.84 (m, 1H), 3.30 (m, 2H), 3.18 (m, 1H), 3.04–2.91 (m, 2H), 2.72 (m, 1H), 2.68 (s, 3H), 2.27 (m, 2H), 2.07–1.61 (m, 8H). MS APCI, m/z=660 (M$^+$). Analysis for C$_{36}$H$_{35}$N$_3$O$_3$SCl$_2$·1.0C$_6$H$_8$O$_7$·2.0H$_2$O. Calculated: C, 56.75; H, 5.33; N, 4.72. Found: C, 56.50; H, 5.26; N, 4.43.

The requisite 1i was prepared as follows.

1a

To a stirred solution of 3-cyano-2-methoxy-1-naphthoic acid (0.506 g, 2.22 mmol) and DCM (28 mL) was added oxalyl chloride (0.24 mL, 2.78 mmol) and 2 drops of DMF. After 2 h at RT toluene (10 mL) was added and the solvent removed in vacuo and the residue set under vacuum pump pressure for 2 h. The crude 3-cyano-2-methoxy-1-naphthalenecarbonyl chloride (1a) was used without purification.

1b

A stirred solution of (S)-2-(3,4-dichlorophenyl)-4-hydroxybutylamine (0.518 g, 2.22 mmol) in DCM (20 mL) was treated with 10% NaOH (2.67 mL) and cooled to 0° C. A solution of 1a (2.22 mmol) in DCM (10 mL) was added and the stirred reaction allowed to warm in the ice bath to RT overnight. The reaction was partitioned between additional DCM and water, the organic phase separated, washed with water, dried (Na$_2$SO$_4$) and the solvent removed in vacuo. The crude material was purified by gradient chromatography (0.5%, 2.0%, 5.0% MeOH/DCM) to give 1b (0.95 g, 97%) as a white solid. $^1$H NMR (300 MHz, CDCl$_3$) δ 8.16 (s, 1H), 7.82 (d, 1H), 7.65–7.32 (m, 5H), 7.14 (dd, 1H), 6.18 (t, 1H), 3.98 (s, 3H), 3.8–3.68 (m, 3H), 3.54 (m, 1H) 3.18 (m, 1H), 2.05 (m, 1H), 1.77 (m, 1H), MS APCI, m/z=443 (M$^+$).

1c

To a stirred solution of 1b (5.51 g, 12.46 mmol) and DCM (100 mL) was successively added tert-butyldimethylsilylchloride (2.82 g, 18.69 mmol), 4-dimethylaminopyridine (0.076 g, 0.623 mmol), and triethylamine (2.78 mL, 19.94 mmol) and the reaction mixture stirred at RT overnight. The mixture was partitioned between additional DCM and water, the organic layer was collected, washed with water and dried (Na$_2$SO$_4$). The crude product was purified by gradient chromatography (eluting with 70%, 50% hexane/Et$_2$O) to yield 1c (6.48 g, 94%) as a white solid. $^1$H NMR (300 MHz, CDCl$_3$) δ8.2 (s, 1H), 7.82 (d, 1H), 7.62–7.36 (m, 51), 7.16 (dd, 1H), 6.14 (t, 1H), 4.01 (s, 3H), 3.88–3.78 (m, 2H), 3.64 (m, 1H), 3.47 (m, 1H), 3.20 (m, 1H), 2.03 (m, 1H), 1.84 (m, 1H), 0.86 (s, 9H), 0.016 (s, 6H). MS APCI, m/z=557 (M$^+$).

1d

A 3-neck flask containing a magnetic stirrer and magnesium chips (0.68 g, 27.96 mmol) was flamed dried and allowed to cool to RT under nitrogen. After the addition of Et$_2$O (30 mL), benzene (15 mL) and iodine (3.55 g, 13.98 mmol), the reaction mixture was heated at reflux for 2 h. After cooling to RT the solution was transferred by cannula to a flask containing 1c (6.48 g, 11.65 mmol) in 108 mL benzene. Heating under reflux was continued for 1 h, the mixture allowed to cool to RT then 1N HCl and DCM were introduced and the mixture stirred for 15 min. The collected organic phase was washed twice with water, dried (Na$_2$SO$_4$) filtered and concentrated. The crude product was purified by gradient chromatography (eluting with 2%, 5%, 10% MeOH/DCM) to give 1d (5.57 g, 88%) as a light yellow solid. $^1$H NMR (300 MHz, CDCl$_3$) δ 11.91 (bs, 1H), 8.15 (s, 1H), 7.77 (m, 1H), 7.45–7.13 (m, 6H), 6.28 (m, 1H), 3.96 (m, 1H), 3.62–3.25 (m, 4H), 1.99 (m, 1H), 1.84 (m, 1H), 0.70 (s, 9H), 0.011 (s, 6H). MS APCI, m/z=543 (M$^+$).

1e

A stirred mixture of 1d (1.50 g, 2.77 mmol), DMF (12.0 mL), K$_2$CO$_3$ (0.574 g, 4.15 mmol) and 2-chloro-ethanol (0.21 mL, 3.11 mmol) was heated at 88° C. for 72 h. and then quenched with aqueous NH$_4$Cl. The mixture was partitioned between DCM and water, the organic layer collected, washed twice with water, dried (Na$_2$SO$_4$), filtered and concentrated. The crude orange solid (1.30 g), consisted of product and starting material in a 1:3 ratio (by NMR) and was used in the next step without further purification. $^1$H NMR (300 MHz, CDCl$_3$) δ 8.22 (s) 1e, δ 8.20 (s) 1d. MS APCI, m/z=587 (M$^+$) 1e.

1f

To a stirred solution of the above 1e/1d mixture (1.30 g) and DCM (20 mL) was added triethylamine (0.47 mL, 2.48 mmol), the mixture cooled to 0° C., and methanesulfonyl chloride (0.19 mL, 2.48 mmol) was added. The mixture partitioned between additional DCM and water, the organic phase collected, washed twice with 1N HCl, twice with saturated aqueous NaHCO$_3$ and dried over Na$_2$SO$_4$. Purification by gradient chromatography (40%, 20% hexane/Et$_2$O) gave if (0.24 g, 13% from 1d) as a white solid. $^1$H NMR (300 MHz, CDCl$_3$) δ 8.24 (s, 1H), 7.86 (dd, 11), 7.58 (m, 2H), 7.47–7.30 (m, 3H), 7.18 (dd, 1H), 6.21 (t, 1H), 4.56 (m, 2H), 4.49 (m, 2H), 3.94–3.81-(m, 2H), 3.66 (m, 1H), 3.48 (m, 1H), 3.21 (m, 1H), 3.16 (s, 3H), 2.03 (m, 1H), 1.85 (m, 1H), 0.86 (s, 9H), 0.026 (s, 6H). MS APCI, m/z=665 (M$^+$).

1g

To a stirred solution of 1f (0.24 g, 0.36 mmol) and THF (12.0 mL) was added 95% NaH (0.010 g, 0.38 mmol) and the mixture refluxed for 40 min. After quenching with NH$_4$Cl, the mixture was partitioned between DCM and water, the organic phase was collected, washed twice with water, dried (Na$_2$SO$_4$), filtered and concentrated. Purification by gradient chromatography (80%, 60%, 20% hexane/Et$_2$O) gave 1g (0.23 g, 71%) as a white solid. $^1$H NMR (300 MHz, CDCl$_3$) δ 8.25 (s, 1H), 7.91–7.82 (m, 2H), 7.64 (t, 1H), 7.54 (t, 1H), 7.39 (m, 2H), 7.16 (dd, 1H), 4.43 (m, 2H), 3.96 (m, 2H), 3.64 (m, 1H), 3.46–3.27 (m, 4H), 2.04 (m, 1H), 1.87 (m, 1H), 0.89 (s, 9H), 0.011 (s, 6H). MS APCI, m/z=569 (M$^+$).

1h

A solution of 1g (0.23 g, 0.397 mmol) in CH$_3$CN (5 mL) was added to stirred 5% HF/CH$_3$CN (4 mL 50% HF/36 mL CH$_3$CN) and the mixture stirred at RT for 40 min. The reaction was quenched by the addition of DCM, water and solid NaHCO$_3$ until pH~6–7 was obtained. The organic phase was collected, washed twice with water, dried (Na$_2$SO$_4$), filtered and concentrated to yield 1h (0.175 g, 97%) as a white solid. $^1$H NMR (300 MHZ, CDCl$_3$) δ 8.25 (s, 1H), 7.97 (d, 1H), 7.84 (d, 1H), 7.65 (t, 1H), 7.54 (t, 1H), 7.41 (m, 2H), 7.17 (dd, 1H), 4.39 (m, 2H), 4.07 (m, 1H), 3.89–3.69 (m, 2H), 3.55 (m, 1H), 3.37–3.29 (m, 3H), 2.11–1.91 (m, 2H), 1.74 (t, 1H). MS APCI m/z=455 (M$^+$).

1i

To a stirred −78° C. solution of oxalyl chloride (0.05 mL, 0.58 mmol) and DCM (8 mL) was added a solution of DMSO (0.08 mL, 1.16 mmol) in DCM (4 mL). After stirring for 5 min a solution of 1h (0.175 g, 0.385 mmol) in DCM (6 mL) was added. After stirring for 15 min, triethylamine (0.32 mL, 2.31 mmol) was added. The mixture was stirred an addition 15 min in the bath, the bath removed and stirring continued at ambient temperature for an additional 2 h. The reaction mixture was partitioned between DCM and a large volume of water, the organic phase collected, washed with an additional large volume of water, the organic phase dried (Na$_2$SO$_4$), filtered and concentrated. Gradient chromatography (1%, 20%, 50% Et$_2$O/DCM) yielded 0.148 g, (84%) of white solid 1i. $^1$H NMR (300 MHz, CDCl$_3$) δ9.80 (s, 1H), 8.26 (s, 1H), 7.93–7.83 (m, 2H), 7.64 (t, 1H), 7.54 (t, 1H), 7.43 (m, 2H), 7.18 (dd, 1H), 4.42 (m, 2H), 3.95 (m, 2H), 3.75–3.75 (m, 1H), 3.40 (m, 2H), 3.10–2.90 (m, 2H). MS APCI, m/z=453 (M$^+$).

Example 2

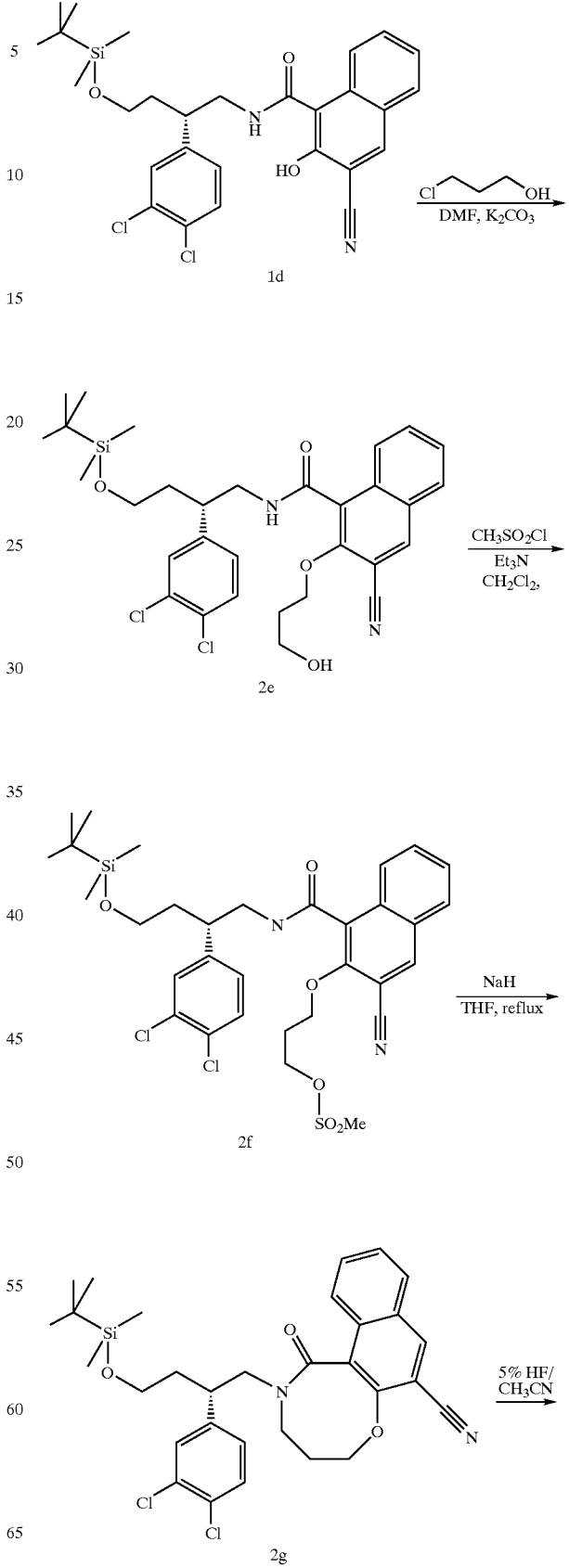

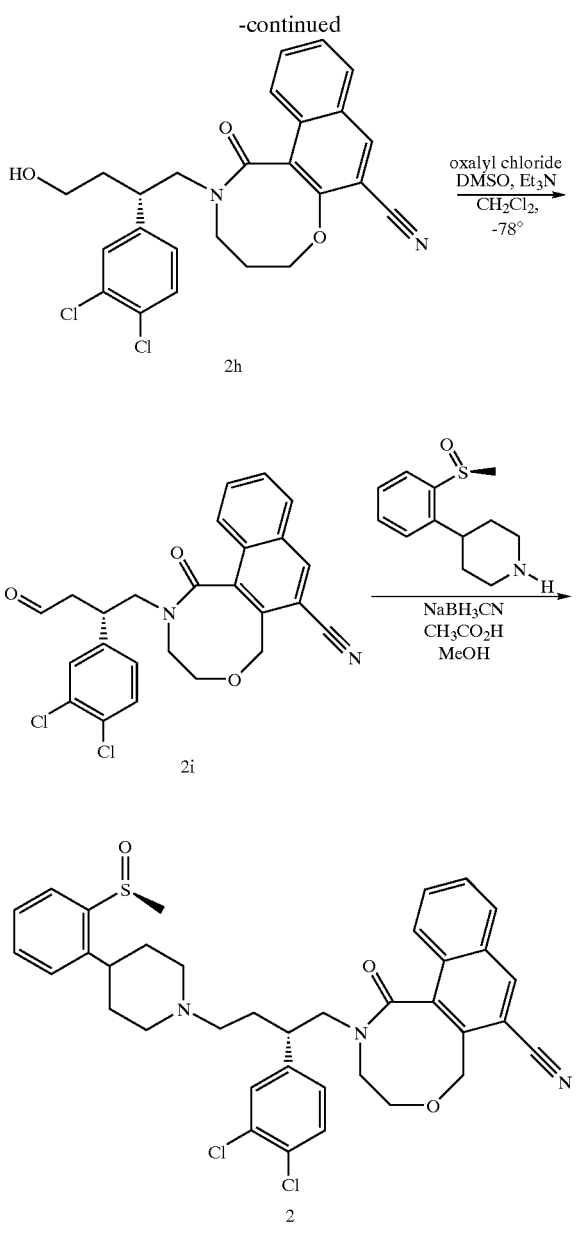

and K₂CO₃ (1.621 g, 11.73 mmol) was heated at 88° C. for 48 h. The reaction was worked up as described for 1e yielding material that had a 2e:1d ratio of 1:2 (¹H NMR). This material was resubjected to the same reaction conditions described above returning material with a 2e:1d ratio of 42:58 (¹H NMR). This material was used in the next step without purification. ¹H NMR (300 MHz, CDCl₃) ratio determined by integration comparison of the amide proton of 1d at δ6.31 (t) and the amide proton of 2e at δ6.20 (t). MS APCI, m/z=601 (M⁺) for 2e m/z=543 (M⁺) for 1d.

2f

The above 2e:1d mixture (4.11 g) was reacted with methanesulfonyl chloride (0.64 mL, 8.19 mmol) as described for 1f. Purification by gradient chromatography (40%, 20% hexane/Et₂O) returned 2f (0.89 g, 17% based on 1d) as a white solid. ¹H NMR (300 MHz, CDCl₃) δ 8.19 (s, 1H), 7.82 (m, 1H), 7.54 (m, 2H), 7.46–7.37 (m, 3H), 7.16 (dd, 1H), 6.10 (t, 1H), 4.50 (t, 2H), 4.33–4.25 (m, 2H), 3.90–3.80 (m, 2H), 3.64 (m, 1H), 3.44 (m, 1H), 3.14 (m, 1H), 3.08 (s, 3H), 2.27–2.20 (m, 2H), 1.99 (m, 1H), 1.79 (m, 1H), 0.83 (s, 9H), −0.025 (s, 6H). MS APCI, m/z=679 (M⁺).

2g

Using the procedure described in the preparation of 1g, 2f (0.890 g, 1.31 mmol) in THF (36.0 mL) was reacted with 90% NaH (0.035 g, 1.39 mmol). Purification by gradient chromatography (80%, 60% hexane/Et₂O) gave 2g (0.411 g, 54%) as a white solid. ¹H NMR (300 MHz, CDCl₃) δ 8.19–8.12 (m, 1H), 7.70 (m, 1H), 7.54–7.34 (m, 4H), 7.24 (m, 1H), 6.64 (m, 1H), 4.88–4.59 (m, 2H), 4.19 (m, 1H), 3.62 (m, 1H), 3.49–3.07 (m, 5H), 2.20–1.83 (m, 4H), 0.88 (s, 9H), 0.11 (s, 6H). MS APCI, m/z=583 (M⁺).

2h

Using the desilylation conditions described in the preparation of 1h, 2g (0.411 g, 0.706 mmol) was reacted with 5% HF/CH₃CN (7 mL 50% HF/63 mL CH₃CN) to yield 2h (0.316 g, 95%) as a white solid. No purification was required. ¹H NMR (300 MHz, CDCl₃) δ 8.21–8.10 (m, 1H), 8.01–7.34 (m, 5H), 7.25 (m, 1H), 6.65 (m, 1H), 4.83–4.58 (m, 2H), 4.20–4.13 (m, 1H), 3.69 (m, 1H), 3.50–2.72 (m, 5H), 2.17–1.80 (m, 4H), 1.45 (m, 1H). MS APCI, m/z=469 (M⁺).

2i

Using the standard Swern oxidizing conditions described in the preparation of 1i, 2h (0.271 g, 0.580 mmol) was converted to, following gradient chromatography (1%, 20%, 50% Et₂O/DCM), 0.261 g (96%) of 2i as a white solid. ¹H NMR (300 MHz, CDCl₃) δ 9.79 (m, 1H), 8.28–8.25 (m, 1H), 7.98–7.37 (m, 5H), 7.25 (m, 1H), 6.68 (m, 1H), 4.8–4.57 (m, 2H), 4.22–4.15 (m, 1H), 3.92–3.36 (m, 3H), 3.17–2.88 (m, 3H), 2.19–1.97 (m, 2H). MS APCI, m/z=467 (M⁺).

4-[(S)-2-methylsulfinyl-phenyl]-piperidine (0.134 g, 0.560 mmol) was reacted with 2i (0.261 g, 0.560 mmol) in the presence of sodium cyanoborohydride under the standard reductive amination conditions described in the preparation of 1. The crude product was purified by gradient chromatography (2%, 5% MeOH/DCM) to yield 2 (0.271 g, 72%) as a white solid which was converted to the citrate salt. ¹H NMR (300 MHz, CDCl₃) δ 8.20–8.14 (m, 1H), 7.98 (m, 1H), 7.81–7.70 (m, 1H), 7.53–7.33 (m, 7H), 7.25 (m, 1H), 6.72 (m, 1H), 4.83–4.58 (m, 2H), 4.17 (m, 1H), 3.60–3.32 (m, 2H), 3.14–2.91 (m, 3H), 2.79 (m, 1H), 2.68 (s, 3H), 2.33–2.26 (m, 2H), 2.19–1.63 (m, 11H). MS APCI, m/z= 674. Analysis for C₃₇H₃₇N₃O₃SCl₂.1.0 C₆H₈O₇.1.8H₂O. Calculated: C, 57.43; H, 5.44; N, 4.67. Found: C, 57.43; H, 5.36; N, 4.49.

The requisite 2i was prepared as follows.

2e

A stirred mixture of 1d (4.24 g, 7.82 mmol), 3-chloropropanol (0.74 mL, 8.80 mmol), DMF (40.0 mL)

Example 3

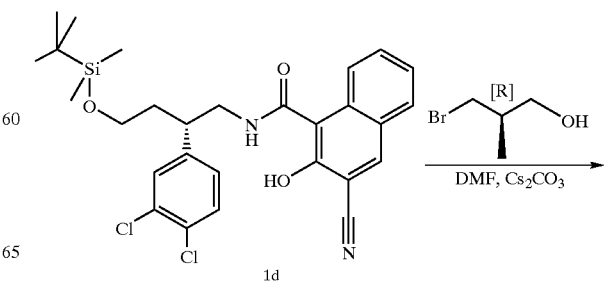

19

-continued

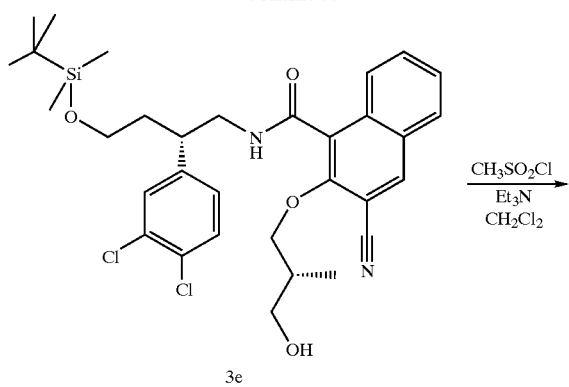

3e

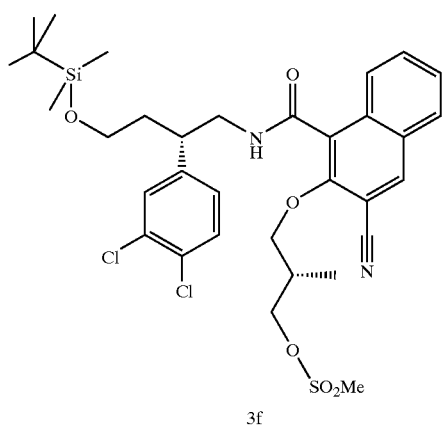

3f

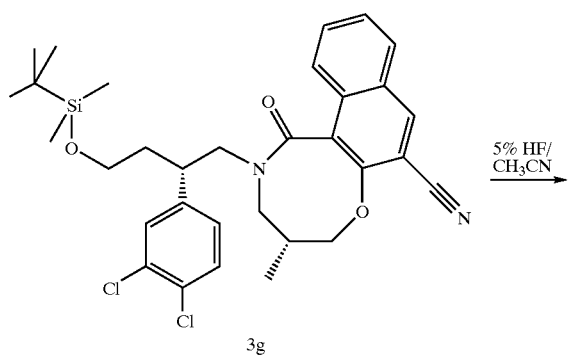

3g

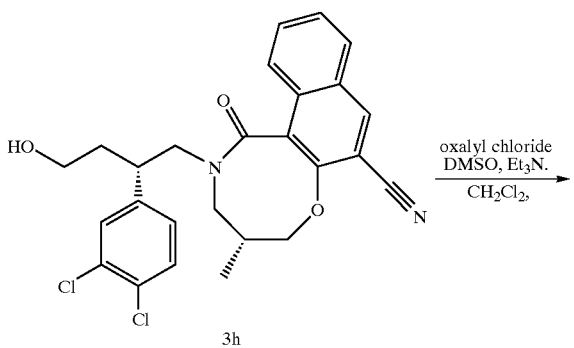

3h

20

-continued

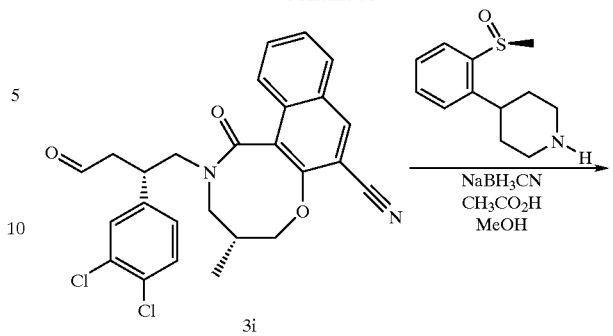

3i

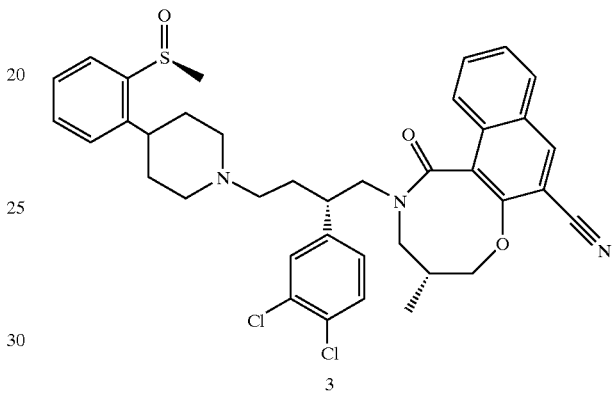

3

4-[(S)-2-Methylsulfinyl-phenyl]-piperidine (0.089 g, 0.374 mmol) was reacted with 3i (0.18 g, 0.374 mmol) in the presence of sodium cyanoborohydride under the standard reductive amination conditions described for 1i. The crude product was purified by gradient chromatography (eluting with 2%, 3%, 5% MeOH/DCM) to give 3 (0.197 g, 77%) as a white solid which was converted to the citrate salt. $^1$H NMR (300 MHz, CDCl$_3$) δ8.15 (s, 1H), 7.98 (m, 1H), 7.74 (m, 1H), 7.49–7.43 (m, 5H), 7.35–7.25 (m, 3H), 6.73 (m, 1H), 4.82 (t, 1H), 4.65 (dd, 1H), 3.83 (m, 1H), 3.34–2.92 (m, 6I), 2.74 (m, 1H), 2.68 (s, 3H), 2.35–2.28 (m, 3H), 2.02–1.67 (m, 8H), 1.00 (d, 3H). MS APCI, m/z=688 (M$^+$). Analysis for C$_{38}$H$_{39}$N$_3$O$_3$SCl$_2$.1.0 C$_6$H$_8$O$_7$.2.0 H$_2$O. Calculated: C, 57.64; H, 5.60; N, 4.58. Found: C, 57.39; H, 5.43; N, 4.46.

The requisite 3i was prepared as follows.

3e

A mixture of 1d (1.28 g, 2.36 mmol), DMF (20 mL), Cs$_2$CO$_3$ (0.962 g, 2.95 mmol) was stirred for 35 min at RT, R-(−)-3-bromo-2-methyl-1-propanol (0.28 mL, 2.60 mmol) added and the mixture heated at 104° C. for 2 h. After cooling to RT a second portion of R-(−)-3-bromo-2-methyl-1-propanol (0.28 mL, 2.60 mmol) was added and the mixture heated overnight at 104° C. The reaction mixture was quenched with NH$_4$Cl and worked up as described for 1e. The crude product was purified by gradient chromatography (eluting with 5%, 10%, 30%, 50% Et$_2$O/DCM) to yield 3e (0.822 g, 57%) as a light yellow solid. $^1$H NMR (300 MHz, CDCl$_3$) δ 8.22 (s, 1H), 7.85 (m, 1H), 7.59 (m, 1H), 7.48 (m, 1H), 7.37 (m, 2H), 7.18 (dd, 1H), 6.21 (t, 1H), 4.27–4.17 (m, 2H), 4.0–3.64 (m, 5H), 3.47 (m, 1H), 3.19 (m, 1H), 2.72 (m, 1H), 2.17–2.0 (m, 2H), 1.84 (m, 1H), 1.16 (d, 3H), 0.88 (s, 9H), 0.014 (s, 6H). MS APCI, m/z=615 (M$^+$).

3f

Using the conditions described in the preparation of 1f, 3e (1.39 g, 2.264 mmol) was reacted with methanesulfonyl chloride (0.20 mL, 2.54 mmol). The crude product was purified by gradient chromatography (40%, 20% hexane/Et$_2$O) to yield 3f (1.41 g, 90%) as a white solid. $^1$H NMR (300 MHz, CDCl$_3$) δ 8.22 (s, 1H), 7.85 (m, 1H), 7.63–7.54 (m, 2H), 7.49–7.36 (m, 3H), 7.18 (dd, 1H), 6.14 (t, 1H), 4.46–4.34 (m, 2H), 4.25–4.14 (m, 2H), 3.93–3.88 (m, 2H), 3.67 (m, 1H), 3.48 (m, 1H), 3.18 (m, 1H), 3.11 (s, 3H), 2.44 (m, 1H), 2.03 (m, 1H), 1.85 (m, 1H), 1.20 (d, 3H), 0.87 (s, 9H), 0.13 (s, 6H). MS APCI, m/z=693 (M$^+$).

3g

To a stirred solution of 3f (1.41 g, 2.04 mmol) in THF (30.0 mL) was added 60% NaH (0.082 g, 2.04 mmol) and the mixture refluxed for 6 h and allowed to stir and cool in the bath to RT overnight. The reaction was worked up as described in the preparation of 1g. Purification by gradient chromatography (80%, 70% hexane/Et$_2$O) gave 3g (0.498 g, 38%) as a white solid. $^1$H NMR (300 MHz, CDCl$_3$) δ 8.13 (s, 1H), 7.71 (m, 1H), 7.50–7.36 (m, 4H), 7.26 (m, 1H), 6.65 (m, 1H), 4.83 (t, 1H), 4.65 (m, 1H), 3.82 (m, 1H), 3.61 (m, 1H), 3.40 (m, 1H), 3.31–3.10 (m, 4H), 2.36 (m, 1H), 1.98–1.84 (m, 2H), 0.98 (d, 3H), 0.89 (s, 9H), 0.015 (s, 6H). MS APCI, m/z=597 (M$^+$).

3h

Using the desilylation conditions described in the preparation of 1h, 3g (0.493 g, 0.826 mmol) was reacted with 5% HF/CH$_3$CN (8.25 mL HF/74.33 mL CH$_3$CN). Purification by gradient chromatography (0.5%, 1.0% MeOH/DCM) gave 3h (0.345 g, 87%) as a white solid. $^1$H NMR (300 MHz, CDCl$_3$) δ 8.13 (s, 1H), 7.72 (m, 1H), 7.48–7.36 (m, 4H), 7.25 (m, 1H), 6.67 (m, 1H), 4.83 (t, 1H), 4.63 (m, 1H), 3.82 (m, 1H), 3.68 (m, 1H), 3.44 (m, 1H), 3.32–3.11 (m, 4H), 2.34 (m, 1H), 2.07–1.86 (m, 2H), 1.51 (m, 1H), 0.98 (d, 3H). MS APCI, m/z=483 (M$^+$). Analysis for C$_{26}$H$_{24}$N$_2$O$_3$Cl$_2$.0.5 H$_2$O. Calculated: C, 63.42; H, 5.11; N, 5.68. Found: C, 63.37; H, 4.95; N, 5.65.

3i

Compound 3h (0.24 g, 0.497 mmol) was reacted with oxalyl chloride/DMSO under the standard Swern oxidizing conditions described in the preparation of 1i. Following gradient chromatography (1%, 20%, 50% Et$_2$O/DCM) 3i (0.20 g, 84%) was obtained as a white solid. $^1$H NMR (300 MHz, CDCl$_3$) δ 9.79 (s, 1H), 8.15 (s, 1H), 7.73 (m, 1H), 7.52–7.37 (m, 4H), 7.25 (m, 1H), 6.69 (m, 1H), 4.78 (t, 1H), 4.63 (dd, 1H), 3.83 (m, 1H), 3.65 (m, 1H), 3.27 (m, 2H), 3.17 (m, 1H), 2.90 (d, 2H), 2.34 (m, 1H), 1.02 (d, 3H). MS APCI, m/z=481 (M$^+$).

Example 4

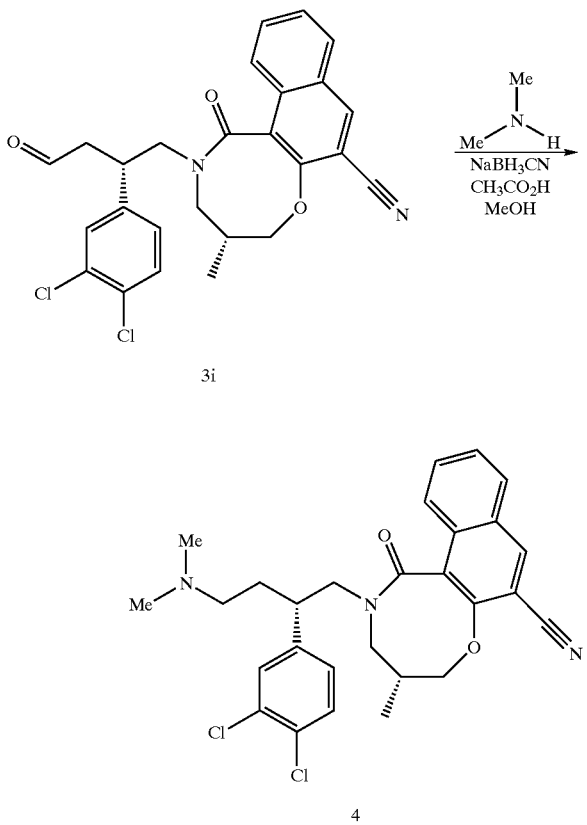

Compound 3i (0.234 g, 0.486 mmol) was reacted with 2M dimethylamine in THF (0.29 mL, 0.583 mmol) in the presence of sodium cyanoborohydride under the reductive amination conditions described in the preparation of 1. The crude product was purified by gradient chromatography (eluting with 2%, 5%, 10% MeOH/DCM) to give 4 (0.214 g, 86%) as a white solid which was converted to the citrate salt. $^1$H NMR (300 MHz, CDCl$_3$) δ 8.13 (s, 1H), 7.71 (m, 1H), 7.53–7.35 (m, 4H), 7.26 (In, 1H), 6.67 (m, 1H), 4.83 (t, 1H), 4.64 (dd, 1H), 3.82 (m, 1H), 3.27–3.05 (m, 4H), 2.35–2.08 (m, 9H), 1.93–1.77 (m, 2H), 0.98 (d, 3H). MS APCI, m/z=510 (M$^+$). Analysis for C$_{28}$H$_{29}$N$_3$O$_2$Cl$_2$.1.0 C$_6$H$_8$O$_7$.1.5 H$_2$O. Calculated: C, 55.97; H, 5.52; N, 5.75. Found: C, 56.08; H, 5.26; N, 5.55.

Example 5

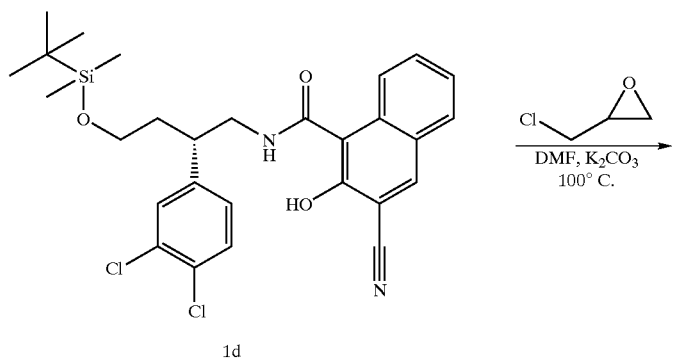

1d

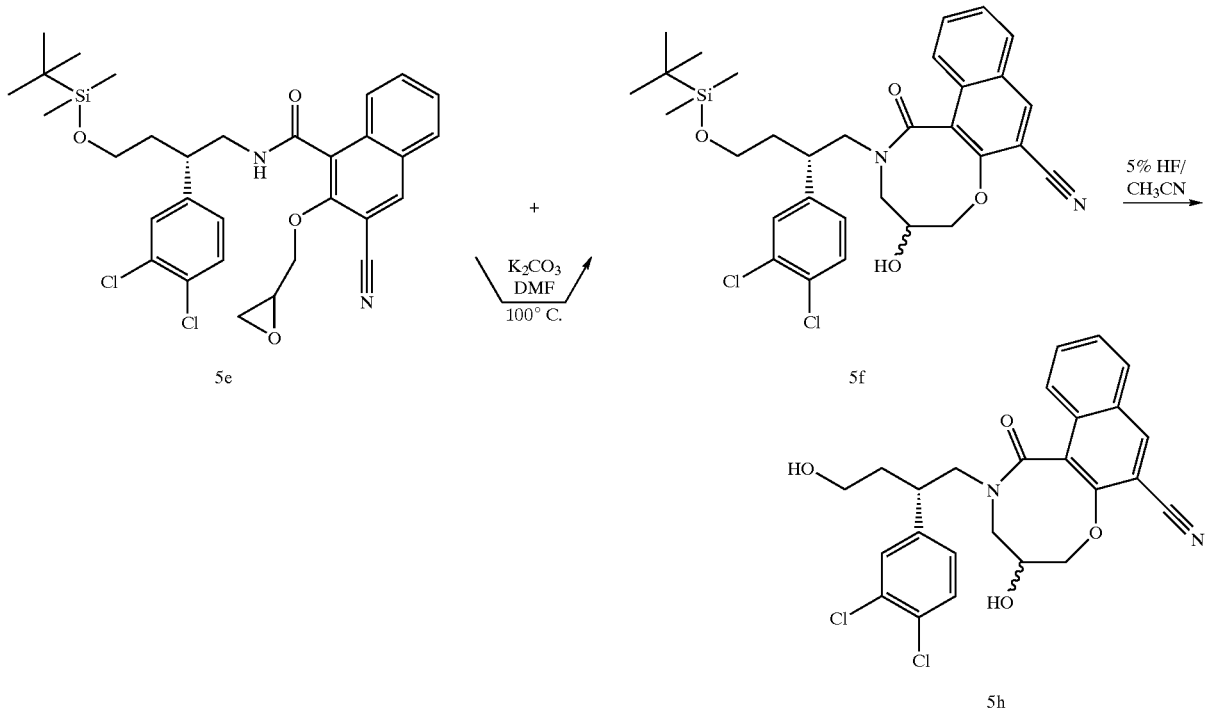

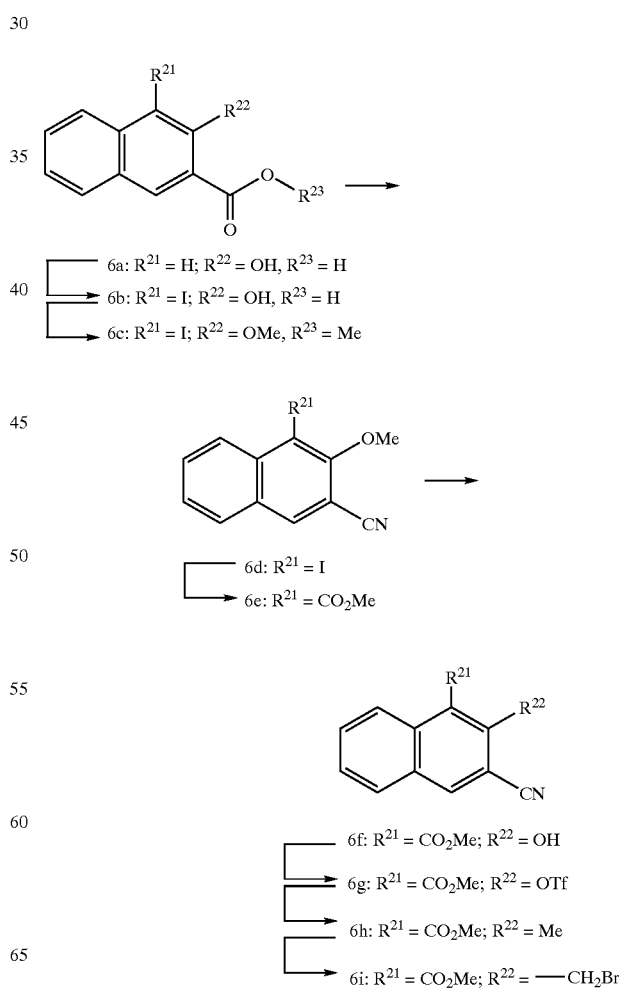

5f

A stirred mixture of 1d (2.505 g, 4.62 mmol), DMF (34 mL), K₂CO₃ (0.958 g, 6.93 mmol), and epichlorohydrin (0.41 mL, 5.197 mmol) was heated in a 100° C. oil bath. Over the course of 6 days of heating the following were added: epichlorohydrin (1.13 equiv./day, 6.8 equiv. total) and K₂CO₃ (1.5 equiv.). The reaction mixture was partitioned between DCM and a large volume of water. The organic was collected, washed twice with large volumes of water, dried (Na₂SO₄) and the solvent removed in vacuo. Purification of crude product by gradient chromatography (eluting with 2.5%, 5.0% Et₂O/DCM) yielded 5e (0.337 g, 12%) as a white solid. $^1$H NMR (300 MHz, CDCl₃) δ 8.21 (s, 1H), 7.85 (m, 1H), 7.62–7.54 (m, 3H), 7.45–7.40 (m, 2H), 7.19 (d, 1H), 6.28 (m, 1H), 4.50 (m, 1H), 4.07 (m, 1H), 3.87–3.81 (m, 2H), 3.65 (m, 1H), 3.49–3.39 (m, 2H), 3.17 (m, 1H), 2.90 (m, 1H), 2.72 (m, 1H), 2.02 (m, 1H), 1.84 (m, 1H), 0.85 (s, 9H), 0.019 (s, 6H), MS APCI, m/z=599 (M⁺) and 5f (0.518 g, 19%) as a white solid. $^1$H NMR (300 MHz, CDCl₃) δ 8.23 (d, 1H), 7.83 (t, 1H), 7.70–7.53 (m, 3H), 7.40 (m, 2H), 7.15 (m, 1H), 4.70 (m, 1H), 4.32–3.12 (m, 9H), 2.23 (m, 1H), 2.02 (m, 1H), 1.87 (m, 1H), 0.86 (s, 9H), 0.80 (s, 6H). MS APCI, m/z=599 (M⁺).

A mixture of 5e (0.337 g, 0.564 mmol) DMF (8.0 mL) and K₂CO₃ (0.078 g, 0.564 mmol) was stirred in a 100° oil bath for 17 h and worked up and purified as above to yield additional 5f (0.188 g, 56% from 5e, total 5f from 1d=0.706 g, 26%).

5h

Using the desilylation conditions described for 1h, 5f (0.704 g, 1.18 mmol) was reacted with 5% HF/CH₃CN (12 mL 50% HF/106 mL CH₃CN). Purification by gradient chromatography (1%, 2%, 5% MeOH/DCM) gave 5h (0.483 g, 85%) as a white solid. $^1$H NMR (300 MHz, CDCl₃) δ 8.24 (d, 1H), 7.85–7.53 (m, 4H), 7.40 (m, 2H), 7.16 (m, 1H), 4.69 (m, 1H), 4.13 (m, 1H), 3.87–3.71 (m, 4H), 3.53–3.25 (m, 4H), 2.35 (m, 1H), 2.07–1.73 (m, 3H). MS APCI, m/z=485 (M⁺).

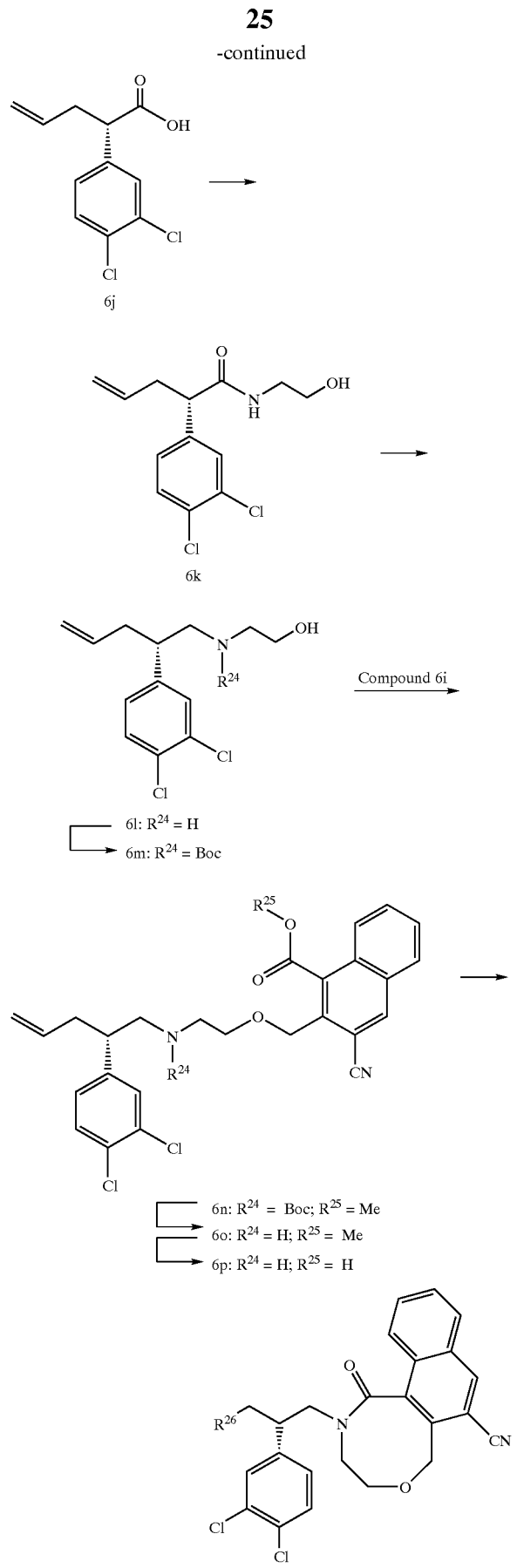

Example 6

A solution of compound 6p (0.78 g), N,N-diisopropylethylamine (0.54 mL) and bis-(2-oxo-3-oxazolidinyl)-phosphinic chloride (0.40 g) in acetonitrile (40 mL) was stirred for 1 h. Additional diisopropylethylamine (0.14 mL) and bis-(2-oxo-3-oxazolidinyl)-phosphinic chloride (0.10 g) were added and the mixture stirred for 0.5 h, concentrated, diluted with EtOAc; washed with 0.5 N HCl, then brine; dried over $MgSO_4$, filtered, concentrated, and purified by flash chromatography using 20–30% EtOAc/hexanes to afford 0.41 g of desired product as a foam solid. $^1$H NMR (300 MHz, $CDCl_3$) δ 8.29 (s), 8.23 (s), 8.04 (d), 7.91 (d), 7.80 (m), 7.66 (t), 7.50 (m), 7.37 (m), 7.28 (m), 7.13 (dd), 6.69 (d), 5.67 (m), 5.11–4.74 (m), 4.62 (m), 4.02–3.68 (m), 3.49–2.98 (m), 2.64–2.43 (m); MS APCI, m/z=465 ($M^+$).

Compound 6p was prepared as follows.

6b

A mixture of NaOH (2.12 g) in methanol (100 mL) was stirred until the solution was homogeneous. Sodium iodide (3.98 g) and compound 6a (5.00 g) were added and stirring continued for 30 min. The resulting suspension was cooled to 0° C. and a 5.25% (w/v) aqueous solution of sodium hypochlorite was added dropwise and stirring continued for 1 h. Saturated sodium thiosulfate (25 mL) was added and after 5 min the solution was acidified to pH 2 by addition of 6 N HCl resulting in the formation of a yellow precipitate which was filtered and washed with water (50 mL). The precipitate was transferred to a round-bottomed flask, dissolved in methanol (70 mL) and toluene (100 mL), concentrated, redissolved in methanol (70 mL), concentrated, redissolved again in methanol (70 mL) and toluene (100 mL) and concentrated to afford the product as a yellow solid (6.26 g). MS m/z 313 (M−1). $^1$H NMR (DMSO-$d_6$): δ 12.41 (broad, 1H), 8.63 (s, 1H), 8.05–7.97 (m, 2H), 7.70 (m, 1H), 7.42 (m, 1H).

6c

A solution of compound 6b (8.0 g), dimethyl sulfate (8.03 g), powdered potassium carbonate (8.80 g), and dry acetone (150 mL) was heated under reflux for 18 h. The solution was cooled to room temperature, triethylamine (15 mL) was added, and stirring continued for 30 min. The solution was filtered through a pad of Celite and washed with dry acetone (50 mL). The filtrate was concentrated to a yellow oil, diluted with EtOAc, and washed successively with 1N HCl (100 mL), saturated aqueous sodium bicarbonate (100 mL), and brine (100 mL). The organic phase was dried (sodium sulfate), filtered, concentrated, and purified by chromatography (0–10% EtOAc in hexanes) to afford the product as a yellow oil (5.53 g). $^1$H NMR (DMSO-$d_6$) δ 8.47 (s, 1H), 8.09 (m, 2H), 7.74 (m, 1H), 7.61 (m, 1H), 3.94 (s, 3H), 3.87 (s, 3H).

6d

Based on the procedure of Wood, J L; Khatri, N A; Weinreb, S M; Tetrahedron Lett; 51, 4907 (1979), compound 6c (5.0 g) was suspended in xylenes (100 mL), cooled to 0° C., dimethylaluminum amide solution (approximately 37 mmol) was added and the solution heated under reflux for 2.5 h. The solution was then cooled to 0° C., acidified to pH 2 by addition of 1N HCl, and extracted with EtOAc (3×100 mL). The combined EtOAc extracts were washed with saturated aqueous sodium bicarbonate (150 mL) and brine (150 mL), dried (sodium sulfate), filtered, concentrated, and purified by chromatography (1:1 EtOAc:DCM, then 10–20% EtOAc in DCM) to afford the product as a white solid (3.29 g). $^1$H NMR (DMSO-d$_6$): δ 8.69 (s, 1H), 8.24–8.04 (m, 2H), 7.91–7.81 (m, 1H), 7.76–7.65 (m, 1H), 3.99 (s, 3H); MS m/z 311 (M+1).

6e

Through a suspension of compound 6d (0.250 g), Pd(OAc)$_2$ (0.018 g), triethylamine (0.081 g) and methanol (20 mL) was bubbled carbon monoxide for 25 min, then stirred at 70° C. under carbon monoxide (1 atm) for 18 h. The cooled solution was filtered, rinsed with methanol (20 mL) and DCM (20 mL), concentrated, preadsorbed onto silica (1 g) and purified by chromatography (0–10% EtOAc in hexanes) to afford the product as a white solid (0.113 g). $^1$H NMR (DMSO-d$_6$): δ 8.78 (s, 1H), 8.12–8.09 (m, 1H), 7.84–7.78 (m, 2H), 7.70–7.63 (m, 1H), 4.02–4.01 (m, 6H); IR (cm$^{-1}$): 2228, 1724, 1296, 1236, 1208, 1017.

6f

A flame dried 250 mL 3-neck flask was charged with magnesium metal (2.42 g, 99.5 mmol). After cooling to room temperature, diethyl ether (80 mL), benzene (30 mL) and iodine (12.62 g, 49.7 mmol) were added. The reaction mixture was heated under reflux for 2 h and the iodine color dissipated. After cooling to room temperature, this solution was transferred to compound 6e (10 g, 41.4 mmol) in benzene (30 mL) via syringe. The flask was washed with benzene (15 mL) and a yellow precipitate formed during the addition. The reaction mixture was heated under reflux for another 1 h. 1N HCl and EtOAc were added and the aqueous layer was extracted with EtOAc. The combined organic layers were washed with saturated Na$_2$S$_2$O$_4$, NaCl, water, dried over MgSO$_4$, filtered and concentrated. The crude product was purified by chromatography (DCM) to afford the product (6.88 g, 73% yield) as a yellow solid. $^1$H NMR (CDCl$_3$) δ 12.82 (s, 1H), 8.81–8.78 (d, 1H), 8.32 (s, 1H), 7.83–7.82 (d, 1H), 7.70 (t, 1H), 7.50 (t, 1H), 4.16 (s, 3H). MS (APCI, negative ion mode) m/z 225.92 (M−).

6g

To a solution of compound 6f (6.24 g, 27.5 mmol) in DCM (140 mL) was added triethylamine (4.21 mL, 30.2 mmol) followed by trifluoromethanesulfonic anhydride (5.05 mL, 30.2 mmol) at 0° C. The mixture was stirred at room temperature for 30 min. Saturated NaHCO$_3$ was added and the aqueous layer was extracted with DCM. The combined organic extracts were dried over MgSO$_4$, filtered and concentrated. The crude product was purified by chromatography (eluting with DCM) to give the product (9.6 g, 97% yield) as a yellow oil. $^1$H NMR (CDCl$_3$) δ 8.44 (s, 1H), 8.29–8.04 (d, 1H), 7.01–7.98 (d, 1H), 7.84 (m, 2H), 4.10 (s, 3H).

6h

A stirred solution of compound 6g (0.28 g, 0.779 mmol), K$_3$PO$_4$ (0.33 g, 1.55 mmol), methylboronic acid (0.096 g, 1.55 mmol) and (1,1'-bis(diphenylphosphino)ferrocene) dichloropalladium (II) CH$_2$Cl$_2$ (64 mg, 0.078 mmol) in THF (8 mL) was heated at 66° C. for 4.5 h. Saturated aqueous NaHCO$_3$ was added and the mixture was extracted with EtOAc (3×). The combined organic layers were dried over MgSO$_4$, filter and concentrated. The crude product was purified by chromatography (eluting with 5%, 8% EtOAc/hexane) to give the product (0.139 g, 78% yield) as a white solid. $^1$H NMR (CDCl$_3$) δ 8.28 (s, 1H), 7.88 (d, 1H), 7.77 (d, 1H), 7.67 (t, 1H), 7.55 (t, 1H), 4.08 (s, 3H), 2.66 (s, 3H). MS m/z 226 (M+).

6i.

A solution of compound 6h (4.8 g), N-bromosuccinimide (15.2 g), and 2,2'-azobis(2-methylpropionitrile) (0.35 g) in carbon tetrachloride (85 mL) was heated under reflux for 3 h. The cooled mixture was diluted with DCM and water and the excess NBS quenched by adding sodium thiosulfate pentahydrate (15.2 g) and stirring for 0.5 h. The layers were separated and the organic washed with water, then brine; dried over MgSO$_4$; filtered; and concentrated under reduced pressure. The crude material was then passed through a plug of silica using 40–60% DCM/hexanes as eluant to afford the desired compound as a white solid (5.2 g). $^1$H NMR (300 MHz, CDCl$_3$) δ 8.33 (s, 1H), 7.90 (m, 2H), 7.69 (m, 2H), 4.82 (s, 2H), 4.13 (s, 3H); MS APCI, m/z=304 (M$^+$).

6k

A solution of compound 6j (Shenvi, A; Jacobs, R T; Miller, S C; Ohnmacht, C J, Jr.; Veale, C A. EP 680962) (2.0 g), diisopropylethyl amine (1.56 mL), ethanolamine (0.59 mL), and 4-dimethylaminopyridine (1.0 g) in DCM (32 mL) was cooled to 5° C. and 1-(3-dimethylaminopropyl)-3-ethylcarbodiimide hydrochloride (1.65 g) was added. The cooling bath was removed and reaction stirred for 50 min, then heated briefly under reflux. After cooling, additional ethanolamine (0.3 mL) was added and stirring continued for 10 min. The mixture was concentrated, diluted with EtOAc; washed with 1 N HCl, then saturated aqueous sodium carbonate, then brine; dried over MgSO$_4$, filtered and concentrated under reduced pressure. The residue was purified by flash chromatography using 30–80% EtOAc/hexanes to afford the desired product (1.0 g) as an oil. $^1$H NMR (300 MHz, CDCl$_3$) δ 7.40 (m, 2H), 7.18 (m, 1H), 5.93 (bs, 1H), 5.68 (m, 1H), 5.05 (m, 2H), 3.64 (m, 2H), 3.40 (m, 3H), 2.84 (m, 1H), 2.48 (m, 1H); MS APCI, m/z=288 (M$^+$).

6l

To a solution of compound 6k (1.5 g) in Et$_2$O (105 mL) was added 13 mL of a 1M solution of lithium aluminum hydride in THF. The mixture was heated under reflux for 3 h. After cooling, 10 mL of saturated aqueous sodium sulfate was cautiously added and the suspension stirred for 0.5 h. Solid sodium sulfate (10 g) was added and the suspension stirred for 0.5 h, filtered through celite, rinsed with EtOAc, concentrated under reduced pressure, and purified by passing through a plug of silica with 3–7% methanol/DCM to afford the desired material (1.25 g) as an oil. $^1$H NMR (300 MHz, CDCl$_3$) δ 7.39 (d, 1H), 7.26 (d, 1H), 7.03 (dd, 1H), 5.64 (m, 1H), 4.98 (m, 2H), 3.55 (t, 2H), 2.71–2.94 (m, 5H), 2.26–2.51 (m, 2H); MS APCI, m/z=274 (M$^+$).

6m

To a solution of compound 6l (1.25 g) in dioxane (10 mL), water (10 mL) and sodium carbonate (0.51 g) was cooled to 0° C. and di-t-butyldicarbonate (1.04 g) was slowly added as a solution in dioxane (5 mL). After 1 h the mixture was diluted with EtOAc, washed with water, then brine; dried over MgSO$_4$; filtered and concentrated under reduced pressure. The resulting residue was passed through a plug of silica to afford 1.4 g of desired product as an oil. $^1$H NMR (300 MHz, CDCl$_3$) δ 7.37 (d, 1H), 7.26 (d, 1H), 7.00 (m, 1H), 5.62 (m, 1H), 5.00 (m, 2H), 3.71–2.94 (m, 7H), 2.34 (m, 2H), 1.41 (s, 9H).

6o

A mixture of compound 6m (1.4 g), compound 6i (1.36 g), and sodium hydride (0.18 g of 60% dispersion in mineral oil) in DMF (6 mL) and THF (6 mL) was stirred overnight. Additional sodium hydride (30 mg of 60% dispersion in mineral oil) was added and the reaction heated at 50° C. for 0.25 h, then at 60° C. for another 0.25 h. The mixture was cooled, diluted with EtOAc, washed with water (twice), then brine; dried over $MgSO_4$, filtered, concentrated under reduced pressure to afford compound 6n which was used without purification. A solution of compound 6n and TFA (10 mL) was stirred in DCM (10 mL), heated under reflux for 20 min, concentrated, diluted with DCM, concentrated again, then purified by flash chromatography using 1–5% methanol/DCM to afford compound 6o (1.5 g) foam solid. $^1$H NMR (300 MHz, $CDCl_3$) δ 8.34 (s, 1H), 7.95 (d, 1H), 7.76 (m, 3H), 7.31 (d, 1H), 7.24 (d, 1H), 7.05 (dd, 1H), 5.55 (m, 1H), 4.98 (m, 2H), 4.76 (d, 2H), 4.03 (s, 3H), 3.83 (t, 2H), 3.42–3.12 (m, 5H), 2.38 (m, 2H); MS APCI, m/z=497 ($M^+$).

6p

A mixture of compound 6o (1.5 g) and pyridine hydrochloride (3.5 g) was heated with stirring in an pre-heated oil bath for 15 min at 180° C. The cooled residue was partitioned with EtOAc and water, washed with 0.5 N HCl, the brine, dried over $MgSO_4$, filtered, concentrated under reduced pressure, then diluted with $Et_2O$ to afford a precipitate which was isolated to afford the product (1.1 g) as a tan solid. $^1$H NMR (300 MHz, $CDCl_3$) δ 9.11 (bs, 1H), 8.17 (s, 1H), 7.98 (d, 1H), 7.82 (d, 1H), 7.73 (t, 1H), 7.62 (t, 1H), 7.40 (d, 1H), 7.27 (d, 1H), 7.11 (dd, 1H), 5.61 (m, 1H), 5.05 (m, 2H), 4.97 (s, 2H), 4.03 (m, 2H), 3.40 (m, 2H), 3.20 (m, 3H), 2.48 (m, 2H); MS APCI, m/z=483 ($M^+$).

Example 7

A stream of ozone was passed through a solution of the material of Example 6 (0.40 g) in methanol (10 mL) and DCM (20 mL) at −78° C. for 5 min and the blue solution color persisted. Stirring was continued for 10 min then nitrogen was bubbled through for 5 min. The reaction warmed to −30° C. then dimethyl sulfide (0.32 mL) was added. The mixture was warmed to room temperature and stirred 1.5 h, concentrated, and purified by flash chromatography using 50–60% EtOAc/hexanes to afford the product (0.30 g) as a foam solid. $^1$H NMR (300 MHz, $CDCl_3$) δ 9.79 (d), 8.31 (s), 8.23 (s), 8.03 (d), 7.92 (d), 7.80 (m), 7.67 (t), 7.59–7.37 (m), 7.28 (m), 7.19 (dd), 6.66 (d), 5.08–4.74 (m), 4.61 (m), 4.05–3.01 (m), 2.96 (d), 2.76 (m); MS APCI, m/z=467 ($M^+$).

Example 8

A solution of the material of Example 7 (0.10 g), triethylamine (0.034 mL), and dimethylamine hydrochloride (23 mg) was dissolved in 2 mL of methanol. Acetic acid was added dropwise until the pH was between 4 and 5. After stirring for 1.5 h sodium cyanoborohydride (23 mg) was added as a solution in 1 mL of methanol in three portions over 10 min and the reaction was allowed to stir for 3 h. It was then concentrated; diluted with EtOAc; washed with water, then brine; dried over $MgSO_4$; filtered; concentrated; then purified by flash chromatography using 6–10% methanol/DCM. Residual triethylamine was removed by dissolving in EtOAc, washing with water, then brine; drying over $MgSO_4$, filtering and concentrating under reduced pressure to afford the product (80 mg) as an oil. This material was converted to the citrate salt by combining with an equimolar amount of citric acid in methanol, then drying. $^1$H NMR (300 MHz, DMSO-$d_6$) δ 8.68 (s), 8.62 (s), 8.09 (d), 8.01 (d), 7.90 (d), 7.82–7.59 (m), 7.40 (m), 6.44 (d), 4.87 (m), 4.71 (t), 4.32 (dd), 3.99 (t), 3.89–3.64 (m), 3.42–2.94 (m), 2.83–2.55 (m), 2.10; MS APCI, m/z=496 ($M^+$).

Example 9

A solution of the material of Example 7 (50 mg), 4-[(S)-2-methylsulfinylphenyl]-piperidine (Shenvi, A B; Jacobs, R T; Miller, S C; Ohnmacht, C J, Jr.; Veale, C A., WO 9516682) (30 mg), and acetic acid (0.012 mL) was stirred in methanol (2 mL) for 0.5 h. Sodium cyanoborohydride (12 mg) was added as a solution in methanol (1 mL) in three portions over 10 min., stirred 2 h, then concentrated under reduced pressure. The residue was diluted with EtOAc; washed with water, then brine; dried over $MgSO_4$, filtered, concentrated, and purified by flash chromatography to afford the product (50 mg) as a solid, then converted to the citrate salt according to the procedure described for Example 8. $^1$H NMR (300 MHz, DMSO-$d_6$) δ 8.68 (s), 8.62 (s), 8.09 (d), 8.01 (d), 7.94–7.36 (m), 6.47 (d), 4.87 (m), 4.72 (t), 4.00 (t), 3.90–3.64 (m), 3.51–1.75 (m); MS APCI, m/z=674 ($M^+$).

Example 10

A solution of the material of Example 7 (50 mg) and sodium borohydride (5 mg) in methanol (2 mL) was stirred for 0.5 h, concentrated, diluted with EtOAc, washed with water, then brine, dried over $MgSO_4$, filtered, concentrated, and purified by flash chromatography using 60–100% EtOAc/hexanes to afford the product (40 mg) as a solid. $^1$H NMR (300 MHz, $CDCl_3$) δ 8.31 (s), 8.23 (s), 8.08 (d), 7.92 (d), 7.80 (m), 7.67 (t), 7.58–7.26 (m), 7.15 (dd), 6.68 (d), 5.09–4.63 (m), 4.02–3.01 (m), 2.62 (m), 1.96 (m); MS APCI, m/z=469 ($M^+$).

Synthesis of Examples 11–14

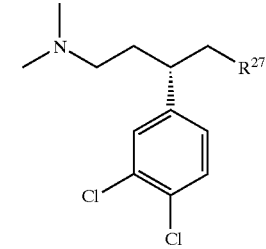

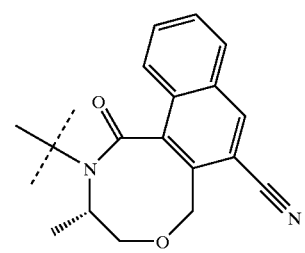

11

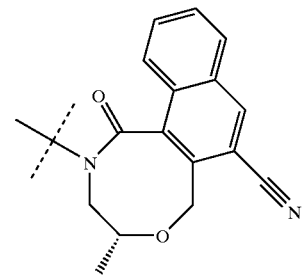

12

| | 13 | 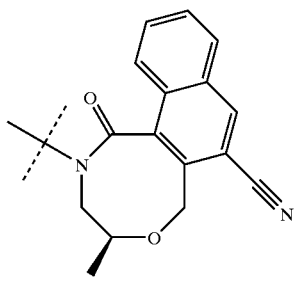 |
|---|---|---|

TABLE 2

| Ex. | MS[a] | HPLC[b] | Salt[c] |
|---|---|---|---|
| 11 | 510.4 | 2.41 | A |
| 12 | 510 | 2.14 | B |
| 13 | 510.3 | 2.50 | A |
| 14 | 510.3 | 2.45 | A |

[a]Mass spectral data; (APCI) m/z. Multiple peaks due to isotopic splitting are not considered; data for the major isotopically abundant signal corresponding to the protonated molecular ion cluster are shown (unless noted otherwise).
[b]HPLC retention time, (min) using Hewlett Packard 1100 HPLC; conditions: initially 95% Solvent A, 5% Solvent B with linear ramp to 10% Solvent A, 90% Solvent B at 3 min, then isocratic at 10% Solvent A, 90% Solvent B until 4 min, then linear ramp to 95% Solvent A, 5% Solvent B at 5 min using flow rate 1.4 mL/min; Solvent A: water containing 0.05% TFA; Solvent B: 90% acetonitrile, 10% water, 0.05% TFA; column: Hewlett Packard SB-C8, 5 micron, 2.1 × 50 mm.
[c]Salt forms: A, tri-fluoroacetate; B, citrate; C, not applicable.

| | 14 | 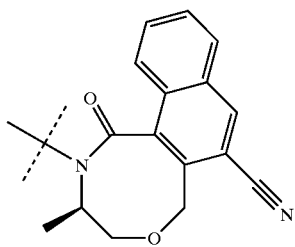 |
|---|---|---|

Compound 11 was prepared according to the procedure described for Compound 8 except (S)-(−)-2-amino-1-propanol was used in place of ethanolamine for the intermediate corresponding to 6k and the amino alcohol was reacted with the acid chloride adduct (prepared from the carboxylic acid using oxalyl chloride) of 6j under Schotten-Baumann conditions. Similarly, compounds 12, 13, and 14 were prepared by using (respectively) (R)-1-amino-2-propanol, (S)-1-amino-2-propanol, or (R)-(−)-2-amino-1-propanol in place of aminoethanol.

TABLE 3

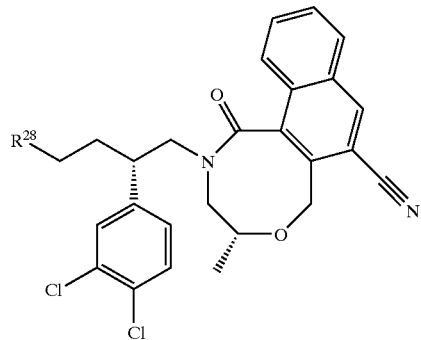

| Example | R[28] | Amine | MS[a] | HPLC[b] | Salt[c] |
|---|---|---|---|---|---|
| 15 | | | 538 | 2.26 | B |
| 16 | -) | | 540 | 2.1 | B |
| 17 | | | 512 | 2.24 | B |
| 18 | | | 526 | 2.46 | A |

TABLE 3-continued

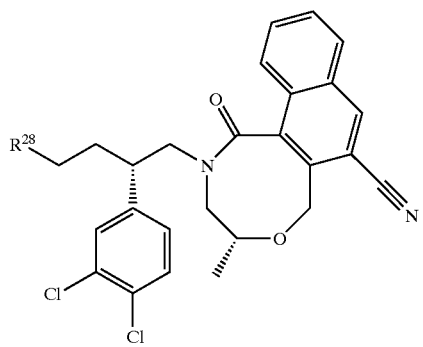

| Example | R[28] | Amine | MS[a] | HPLC[b] | Salt[c] |
|---|---|---|---|---|---|
| 19 | (pyridin-3-ylmethyl)amino- | 3-(aminomethyl)pyridine | 573 | 2.39 | A |
| 20 | 2-(1H-imidazol-4-yl)ethylamino- | 2-(1H-imidazol-4-yl)ethylamine | 576 | 2.33 | A |
| 21 | 2-(1-methylpyrrolidin-2-yl)ethylamino- | 2-(1-methylpyrrolidin-2-yl)ethylamine | 593 | 2.35 | A |
| 22 | N-methyl-2-phenylethylamino- | N-methyl-2-phenylethylamine | 600 | 2.9 | A |
| 23 | (2-methoxybenzyl)amino- | 2-methoxybenzylamine | 602 | 2.85 | A |
| 24 | 3-(dimethylamino)propylamino- | 3-(dimethylamino)propylamine | 567 | 2.33 | A |
| 25 | cyclopropylamino- | cyclopropylamine | 522 | 2.6 | A |
| 26 | (carbamoylmethyl)(methyl)amino- | 2-(methylamino)acetamide | 553 | 2.44 | A |

TABLE 3-continued

[Structure: core scaffold showing a naphtho-fused oxazocine system with pendant 3,4-dichlorophenyl group bearing R²⁸ substituent, and a nitrile group]

| Example | R²⁸ | Amine | MSᵃ | HPLCᵇ | Saltᶜ |
|---------|-----|-------|-----|-------|-------|
| 27 | H₂NSO₂-C₆H₄-CH₂-NH- (4-sulfamoylbenzylamino) | 4-H₂NSO₂-C₆H₄-CH₂-NH₂ | 651 | 2.6 | A |
| 28 | 3,4-dimethoxyphenethyl-NH- | 3,4-dimethoxyphenethylamine | 646 | 2.8 | A |
| 29 | 2-oxopyrrolidin-1-yl-propyl-NH- | 1-(3-aminopropyl)-2-pyrrolidinone | 607 | 2.56 | A |
| 30 | t-Bu-NH- | t-Bu-NH₂ | 538 | 2.68 | A |
| 31 | (Me₂N-CH₂CH₂-N(Me)-) | Me₂N-CH₂CH₂-NHMe | 567 | 2.33 | A |
| 32 | imidazol-1-yl-propyl-NH- | 1-(3-aminopropyl)imidazole | 590 | 2.33 | A |
| 33 | morpholin-4-yl- | morpholine | 552 | 2.55 | A |
| 34 | (tetrahydrofuran-2-yl)methyl-NH- | (tetrahydrofuran-2-yl)methylamine | 566 | 2.64 | A |

TABLE 3-continued

| Example | R²⁸ | Amine | MSᵃ | HPLCᵇ | Saltᶜ |
|---|---|---|---|---|---|
| 35 | benzo[d][1,3]dioxol-5-ylmethyl-NH- | benzo[d][1,3]dioxol-5-ylmethyl-NH₂ | 616 | 2.79 | A |
| 36 | pyrrolidin-1-yl | pyrrolidine (NH) | 536 | 2.61 | A |
| 37 | CF₃CH₂-N(CH₃)- | CF₃CH₂-NH(CH₃) | 564 | 2.49 | A |
| 38 | CH₃OCH₂CH₂-NH- | CH₃OCH₂CH₂-NH₂ | 540 | 2.42 | A |
| 39 | (CH₃)₂NCH₂CH₂-NH- | (CH₃)₂NCH₂CH₂-NH₂ | 553 | 2.27 | A |
| 40 | CH₃O(CH₂)₃-NH- | CH₃O(CH₂)₃-NH₂ | 554 | 2.54 | A |
| 41 | azetidin-1-yl | azetidine (NH) | 522 | 2.49 | A |
| 42 | CH₃SCH₂CH₂-NH- | CH₃SCH₂CH₂-NH₂ | 556 | 2.55 | A |
| 43 | HO(CH₂)₃-NH- | HO(CH₂)₃-NH₂ | 540 | 2.38 | A |

TABLE 3-continued
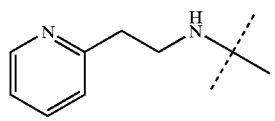
| Example | R²⁸ | Amine | MSᵃ | HPLCᵇ | Saltᶜ |
|---|---|---|---|---|---|
| 44 | 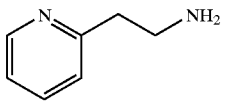 | 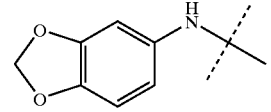 | 587 | 2.33 | A |
| 45 | 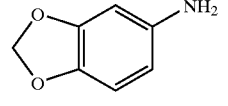 | 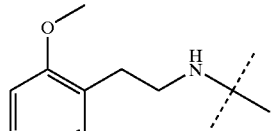 | 602 | 2.57 | A |
| 46 | 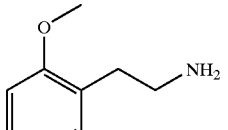 | 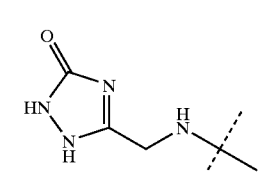 | 616 | 2.68 | A |
| 47 | 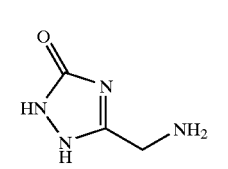 | 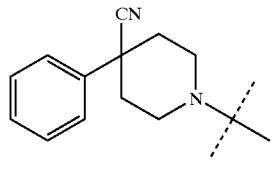 | 579 | 2.17 | A |
| 47 | 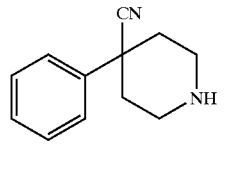 | 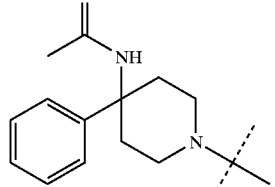 | 651 | 2.66 | A |
| 49 | 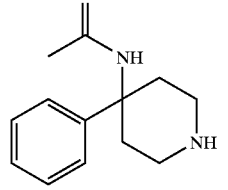 | 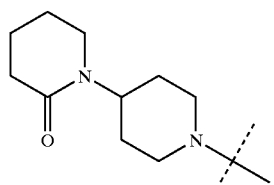 | 683 | 2.48 | A |
| 50 | 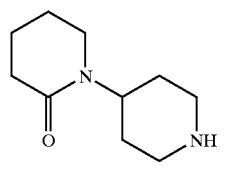 | | 647 | 2.35 | A |

TABLE 3-continued

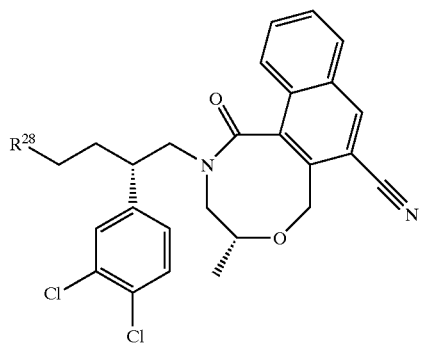

| Example | R[28] | Amine | MS[a] | HPLC[b] | Salt[c] |
|---|---|---|---|---|---|
| 51 | (methylamino-t-butyl) | (isopropylamine) | 496 | 2.27 | A |
| 52 | (4-hydroxy-4-phenylpiperidinyl) | (4-hydroxy-4-phenylpiperidine) | 642 | 2.53 | A |
| 53 | (cyclopropylmethylamino) | (cyclopropylmethylamine) | 536 | 2.44 | A |
| 54 | (piperidinyl) | (piperidine) | 550 | 2.42 | A |
| 55 | (4-methylpiperazinyl) | (1-methylpiperazine) | 565 | 2.13 | A |
| 56 | (4-phenylpiperidinyl) | (4-phenylpiperidine) | 626 | 2.71 | A |
| 57 | (aminoethylamino) | (ethylenediamine) | 525 | 2.09 | A |

(Refer to legend for Table 2)

Synthesis of Examples 15–57

Compounds 15–57 were prepared according to the procedure described for Compound 12 except the aldehyde was reacted with the amine indicated in Table 3 in place of dimethyl amine. Each compound was purified by reverse phase HPLC.

43

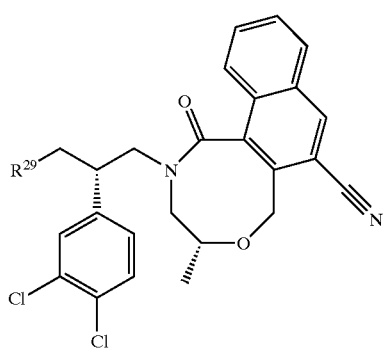

58a: R²⁹ = H₂C=CH—
58b: R²⁹ = HC(O)—
58: R²⁹ = HOOC—

44

Example 58

Compound 58a was prepared according to the procedure described for Compound 6 except (R)-1-amino-2-propanol was used in place of ethanolamine for the intermediate corresponding to 6k and the amino alcohol was reacted with the acid chloride adduct (prepared from the carboxylic acid using oxalyl choride) of 6j under Schotten-Baumann conditions. Compound 58a was oxidized to aldehyde 58b using osmium tetroxide/sodium peroidate, then oxidized to the carboxylic acid 58 using Jones reagent. HPLC: 2.62 min, MS, m/e=497.4 (see Table 2 legend for details).

TABLE 4

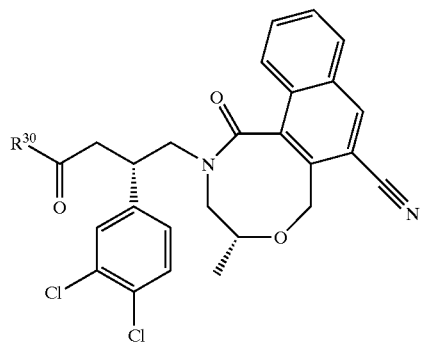

59–70

| Example | $R^{30}$ | Amine | MS$^a$ | HPLC$^b$ |
|---|---|---|---|---|
| 59 | H₂N— | † | 496.2 | 2.29 |
| 60 | (CH₃)₂N— | (CH₃)₂NH | 524.3 | 2.53 |
| 61 | H₂N-CH₂CH₂-NH— | H₂N-CH₂CH₂-NH₂ | 539.3 | 2.04 |
| 62 | (CH₃)₂N-CH₂CH₂-N(CH₃)— | (CH₃)₂N-CH₂CH₂-NHCH₃ | 581.4 | 2.25 |
| 63 | 4-pyridyl-CH₂-NH— | 4-pyridyl-CH₂-NH₂ | 587.3 | 2.11 |

TABLE 4-continued
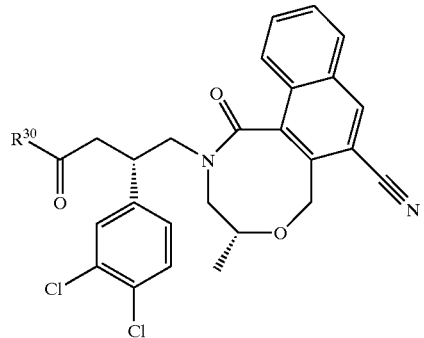
59–70
| Example | R³⁰ | Amine | MSª | HPLCᵇ |
|---|---|---|---|---|
| 64 | 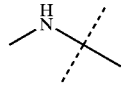 |  | 510.4 | 2.51 |
| 65 | 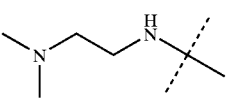 | 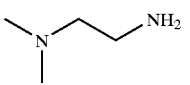 | 567.47 | 2.22 |
| 66 | 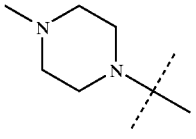 | 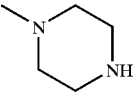 | 579.47 | 2.29 |
| 67 | 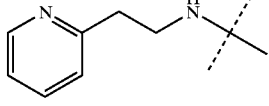 | 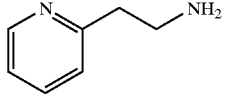 | 601.47 | 2.24 |
| 68 | 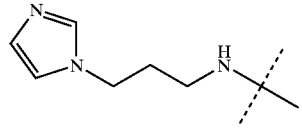 | 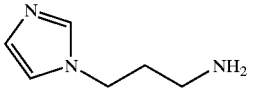 | 604.49 | 2.21 |
| 69 | 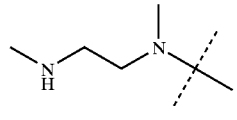 | 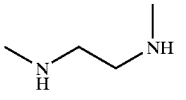 | 567.49 | 2.29 |
| 70 | 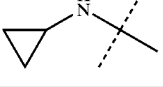 |  | 536.45 | 2.61 |
Compounds 61–63 and 65–69 were TFA salts. (Refer to legend for Table 2)
† Prepared by reaction with ammonium hydroxybenzotriazole according to Bajusz, S; et al.; Fed. Eur. Biochem. Soc.; 1977, 76, 91.

Synthesis of Compounds 59–70

Compounds 59–70 were prepared by reaction of the corresponding acid chloride derived from 58 with the amines indicated in Table 4 in DCM, then purified by reverse phase HPLC. The requisite acid chloride was prepared from 58 with oxalyl chloride in DCM using standard conditions, dried under vacuum, and used without purification.

TABLE 5

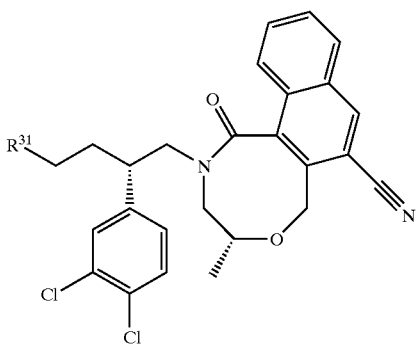

| Example | $R^{31}$ | $MS^a$ | $HPLC^b$ | Synthesis |
|---|---|---|---|---|
| 71 | HO— | 483.4 | 2.82 | Reduction of 58 using $NaBH_4$ |
| 72 | Cl | 501.4 | 3.35 | Chlorination of 71 using hexachloroacetone and $PPh_3$ |
| 73 | Br | 545.3 | 3.4 | Bromination of 71 using $Ph_3PBr_2$ |

(Refer to legend for Table 2)

74

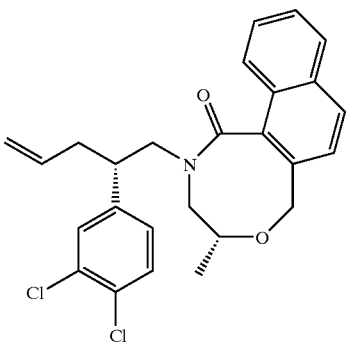

Example 74

Example 74 was prepared according to the method described for 58a except 2-bromomethyl-1-naphthoic acid methyl ester was used in place of 6i, and the methyl ester was hydrolyzed to the carboxylic acid (to afford the compound corresponding to 6p) using LiOH (3.1 equivalents) in water/ethylene glycol at 150° C. overnight instead of using pyridine hydrochloride. HPLC: 3.33 min, MS; m/e=454.42 (see Table 2 legend for details).

TABLE 6

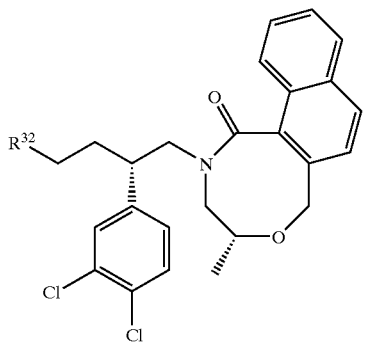

| Example | $R^{32}$ | Amine | $MS^a$ | $HPLC^b$ | $Salt^c$ |
|---|---|---|---|---|---|
| 75 | (structure) | (structure) NH | 485.45 | 2.51 | A |
| 76 | (structure) | (structure) NH | 513.46 | 2.61 | A |
| 77 | (structure) | (structure) $NH_2$ | 487.41 | 2.53 | A |

(Refer to legend for Table 2)

Synthesis of Compounds 75–77

Compounds 75–77 were prepared by reductive amination of the aldehyde (S)-3-(3,4-dichlorophenyl)-4-((R)-9-methyl-12-oxo-7,9,10,12-tetrahydro-8-oxa-11-azacycloocta[α]naphthalen-11-yl)-butyraldehyde with the amines indicated in Table 6 in methanol with sodium cyanoborohydride under conditions similar to those described for the preparation of compound 8, followed by purification by reverse phase HPLC. The requisite aldehyde was prepared by oxidation of 74 using osmium tetroxide/sodium peroidate.

Sulfur Compounds

Intermediate S1: Methyl 3-Cyano-2-{[(trifluoromethyl)sulfonyl]oxy}-1-naphthoate

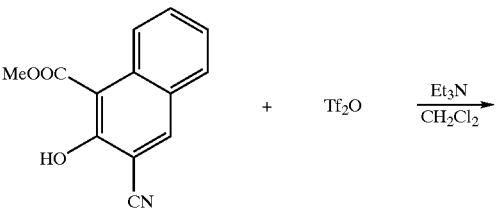

-continued

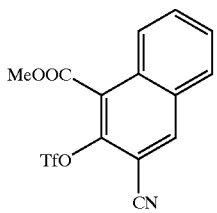

To a solution of methyl 3-cyano-2-hydroxy-1-napthoate (3.1 g, 13.6 mmol) in dry methylene chloride (60 mL) at 0° C. was added triethylamine (2.14 mL, 15.4 mmol) followed by dropwise addition of trifluoromethylsulfonic anhydride. After stirring for an additional 30 min at 0° C. and 30 min at ambient temperature, the reaction mixture was diluted with methylene chloride (60 mL), washed with 0.5 N HCl (2×40 mL) and saturated NaHCO$_3$ (2×40 mL), dried (MgSO$_4$), filtered, and evaporated to dryness. The residue was purified by chromatography on silica gel in methylene chloride to give 3.7 g (75% yield) of the title compound.

Intermediate S2: Methyl 2-({2-[(tert-Butoxycarbonyl)amino]ethyl}thio)-3-cyano-1-naphthoate

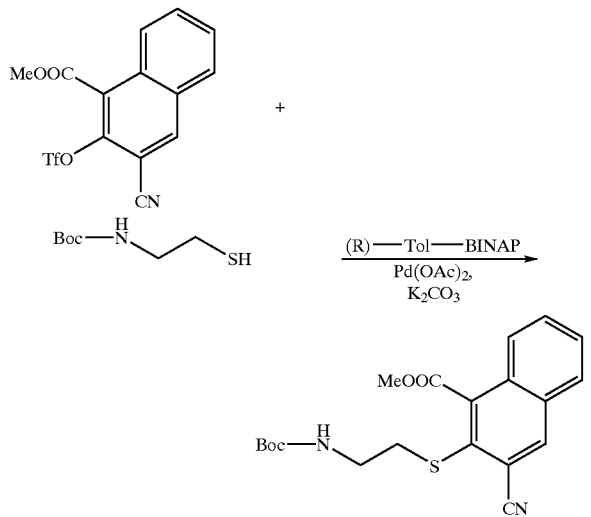

To a suspension (vacuum degassed 3 times) of potassium carbonate (110 mg, 0.78 mmol) in toluene (5 mL) under nitrogen was added tert-butyl 2-mercaptoethylcarbamate (131 µL, 0.78 mmol) followed by stirring at ambient temperature for 1 h. To this suspension was added by cannula a solution (vacuum degassed 3 times) of methyl 3-cyano-2-{[(trifluoromethyl)-sulfonyl]oxy}-1-naphthoate (Intermediate 1, 200 mg, 0.56 mmol), (R)-Tol-BINAP (44.1 mg, 0.07 mmol), and palladium(II) acetate (14 mg, 0.06 mmol) in toluene (10 mL). The resulting suspension was stirred at 80° C. for 20 h, cooled,(reduced volume by ½ under reduced pressure, diluted with ether (12 ml) and methylene chloride (6 ml), washed organic layer with 20% K$_2$CO$_3$ (2×15 ml), water and brine, dried over Na$_2$SO$_4$, filtered, and evaporated to dryness. The residue was precipitated from 10% ethyl acetate in hexanes to give 150 mg of the title compound. An additional 40 mg (88% overall yield) of the title compound was isolated from the mother liquor by chromatography on silica gel in 20% ethyl acetate/hexanes.

Intermediate S3: Methyl 2-[(2-Aminoethyl)thio]-3-cyano-1-naphthoate Hydrochloride

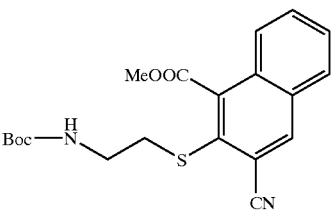

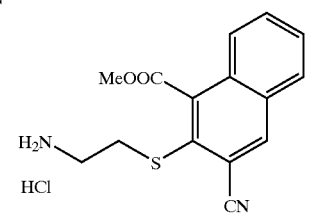

To a solution of methyl 2-({2-[(tert-butoxycarbonyl)amino]ethyl}thio)-3-cyano-1-naphthoate (Intermediate 2, 140 mg, 0.36 mmol) in ethyl acetate (20 mL) cooled to −20° C. was bubbled HCl gas for 5 min. The reaction mixture was allowed to warm to ambient temperature over 2 h and then evaporated to dryness to gave the title compound as an off white solid (115 mg) which was used without further purification.

Intermediate S4: (2S)-2-(3,4-Dichlorophenyl)pent-4-enal

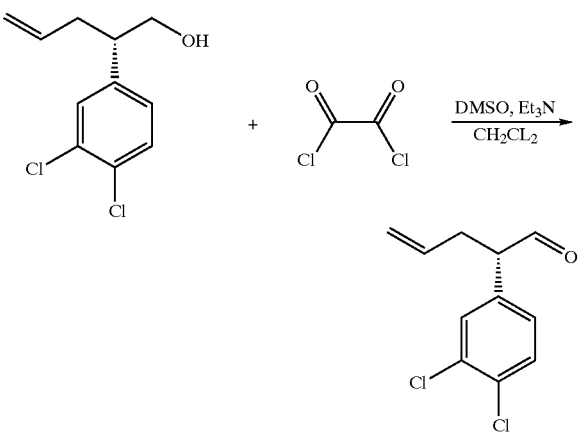

To a solution of oxalyl chloride (0.713 mL, 8.24 mmol) at −78° C. in dry methylene chloride (100 mL) under nitrogen in a three necked flask was added dropwise a solution of DMSO (1.37 mL, 19.8 mmol) in methylene chloride (4 mL) with stirring at −78° C. for an additional 20 min. A solution of (2S)-2-(3,4-dichlorophenyl)pent-4-en-1-ol (1.26 g, 5.45 mmol) in methylene chloride (50 mL) was added dropwise (45 min) while maintaining the reaction temperature below −60° C. After stirring at −60° C. for an additional 2 h, triethylamine (4.6 mL, 33.3 mmol) was added dropwise. The stirred reaction mixture was allowed to warm to ambient temperature for 2 h, cooled in ice, quenched by addition of water (80 mL), and stirred for an additional 30 min. The organic layer was washed with water and brine, dried (Na$_2$SO$_4$), and evaporated to give 1.25 g of the title compound which was used without further purification. This material was determined to be about 72% pure by HPLC.

Intermediate S5: Methyl 3-Cyano-2-[(2-{[(2S)-2-(3,4-dichlorophenyl)pent-4-enyl]amino}ethyl)thio]-1-naphthoate Hydrochloride

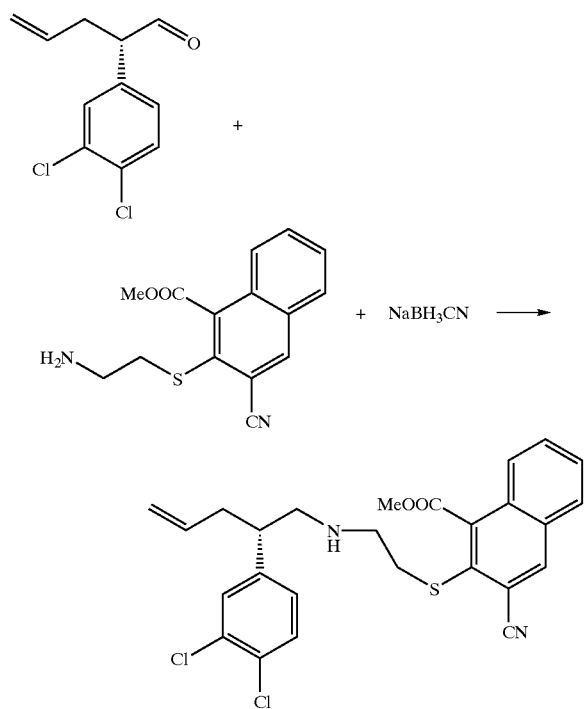

To a solution of methyl 2-[(2-aminoethyl)thio]-3-cyano-1-naphthoate hydrochloride (Intermediate 3, 530 mg, 1.65 mmol) in methanol (100 mL) was added triethylamine (250 μL, 1.82 mmol). After 30 min (2S)-2-(3,4-dichlorophenyl)pent-4-enal {Intermediate 4, 525 mg (72% pure), 1.65 mmol} and the pH was adjusted to 4–5 with acetic acid. After 30 min a solution of sodium cyanoborohydride (200 mg, 3.20 mmol) in methanol (2 mL) was added and reaction mixture stirred at ambient temperature overnight. Reaction mixture volume reduced by half and 20% $K_2CO_3$ (50 mL) was added. Reaction mixture volume reduced further to about 50 mL and methylene chloride (100 mL) was added. The organic layer was washed with brine, dried ($Na_2SO_4$), and evaporated to an oil which was chromatography on silica gel in 5% MeOH/CHCl$_3$ to give 730 mg of the free base. The free base was dissolved in HCl/MeOH and evaporated to dryness to give 780 mg of the title compound.

Intermediate S6: 3-Cyano-2-[(2-{[(2S)-2-(3,4-Dichlorophenyl)pent-4-enyl]amino}ethyl)thio]-1-naphthoic Acid

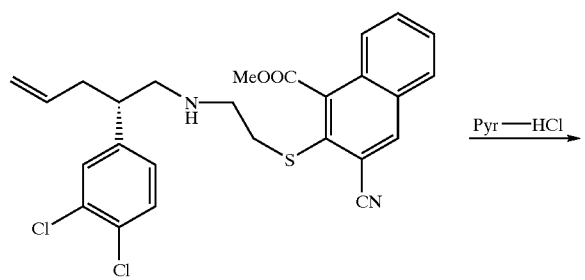

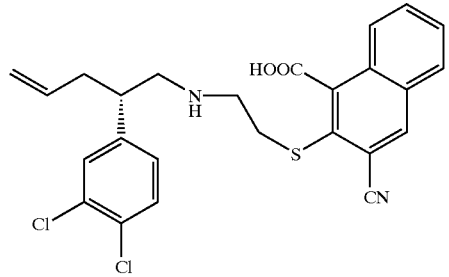

An evenly distributed mixture of methyl 3-cyano-2-[(2-{[(2S)-2-(3,4-dichlorophenyl)pent-4-enyl]amino}ethyl)thio]-1-naphthoate hydrochloride (Intermediate 5, 150 mg, 0.28 mmol) and pyridine hydrochloride (487 mg, 4.20 mmol) was heated at 180° C. for 5 min, cooled, and partitioned between ethyl acetate and water. The organic layer was washed with 1 N HCl and brine, dried (Na$_2$SO$_4$), and evaporated to dryness to give 135 mg (100% yield) of the title compound which was used without further purification.

Example 78
2-[(2S)-2-(3,4-Dichlorophenyl)pent-4-enyl]-1-oxo-1,2,3,4-tetrahydronaphtho[1,2-f][1,4]thiazepine-6-carbonitrile

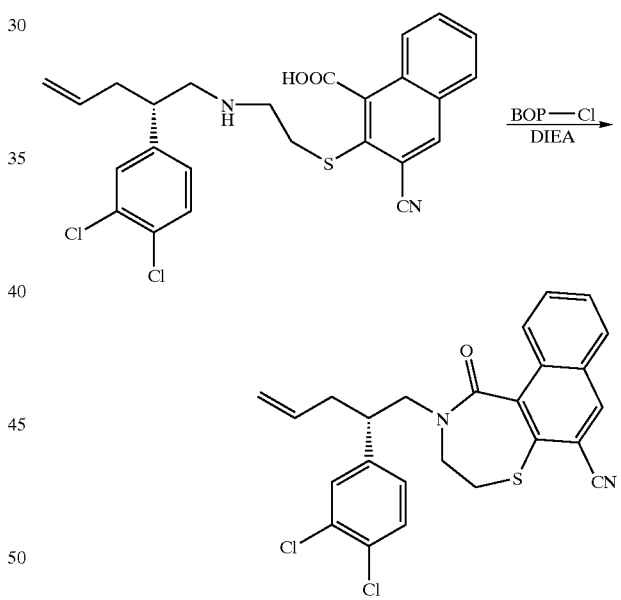

To a solution of 3-cyano-2-[(2-{[(2S)-2-(3,4-Dichlorophenyl)pent-4-enyl]amino}ethyl)thio]-1-naphthoic acid (Intermediate 6, 135 mg, 0.28 mmol) in dry acetonitrile (6 mL) under nitrogen at 0° C. was added diisopropylethyl amine (146 μL, 0.84 mmol) and bis(2-oxo-3-oxazolidinyl)phosphinic chloride (BOP-Cl, 86 mg, 0.34 mmol). Stirring was continued for 45 min as the reaction mixture was allowed to warm to ambient temperature. The reaction mixture was diluted with ethyl acetate (50 mL), washed with 0.5 N HCl and brine, dried (Na$_2$SO$_4$), and evaporated to a residue which was chromatographed on silica gel in 25–40% EtOAc/Hexanes to give 85 mg of partially purified material. A portion (50 mg) of this material was chromatographed on silica gel in 20% EtOAc/Hexanes to give 35 mg of the title compound.

53

Intermediate 78a: 2-[(2S)-2-(3,4-dichlorophenyl)-4-oxobutyl]-1-oxo-1,2,3,4-tetrahydronaphtho[1,2-f][1,4]thiazepine-6-carbonitrile Intermediate 78b: (5S)-2-[(2S)-2-(3,4-dichlorophenyl)-4-oxobutyl]-1-oxo-1,2,3,4-tetrahydronaphtho[1,2-f][1,4]thiazepine-6-carbonitrile 5-oxide Intermediate 78c: (5R)-2-[(2S)-2-(3,4-dichlorophenyl)₄-oxobutyl]-1-oxo-1,2,3,4-tetrahydronaphtho[1,2-f][1,4]thiazepine-6-carbonitrile 5-oxide

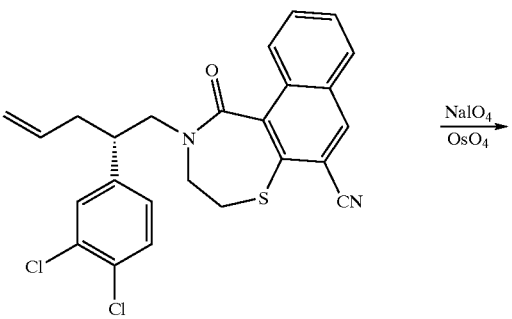

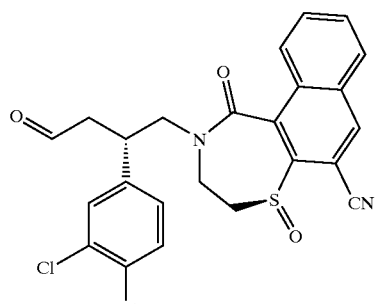

Intermediate 78a

+

Intermediate 78b

+

54

-continued

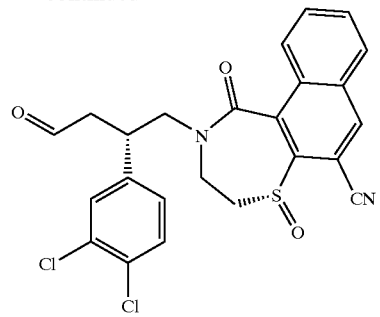

Intermediate 78c *

To a solution of 2-[(2S)-2-(3,4-dichlorophenyl)pent-4-enyl]-1-oxo-1,2,3,4-tetrahydronaphtho[1,2-f][1,4]thiazepine-6-carbonitrile (Example 1, 225 mg, 0.50 mmol) in 3:1 THF/water (10 mL) under nitrogen at 0° C. was added osmium tetroxide (4% in water, 32.5 μL, 0.01 mmol) followed in 10 min by portion wise addition of sodium periodate over 5 min. The reaction mixture was allowed to warm to ambient temperature over 3 h and clarified by the addition of water. The products were extracted into ether and organic layer was washed with saturated NaHCO₃ and brine, dried (Na₂SO₄), and evaporated to 230 mg of an oil which was chromatographed on silica gel in 10% MeOH/CHCl₃ to give 40 mg of intermediate 78a, 22 mg of Intermediate 78b and 11 mg of Intermediate 78c.

Example 79

2-[(2S)-2-(3,4-dichlorophenyl)-4-(dimethylamino)butyl]-1-oxo-1,2,3,4-tetrahydronaphtho[1,2-f][1,4]thiazepine-6-carbonitrile To a solution of Intermediate 7a (40 mg, 0.085 mmol) in methanol (2 mL) under nitrogen was added dimethylamine hydrochloride (11 mg, 0.13 mmol) and triethylamine (15 μL, 0.11 mmol) followed in 10 min by acidic acid (3 drops to adjust pH to between 4 and 5). After stirring the reaction mixture for 30 min at ambient temperature sodium cyanoborohydride (9 mg, 0.1445 mmol) in methanol (1 mL) was added with stirring continued for 1 h. The solvent was evaporated and the residue was dissolved in ethyl acetate (20 mL), washed with water and brine, dried (Na$_2$SO$_4$), and evaporated to give 43 mg of crude product which was chromatographed on ammoniated silica gel in 10–15% MeOH/CHCl$_3$ to give 23 mg of the title compound.

Example 80

(5S)-2-[(2S)-2-(3,4-dichlorophenyl)-4-(dimethylamino)butyl]-1-oxo-1,2,3,4-tetrahydronaphtho[1,2-f][1,4]thiazepine-6-carbonitrile 5-oxide

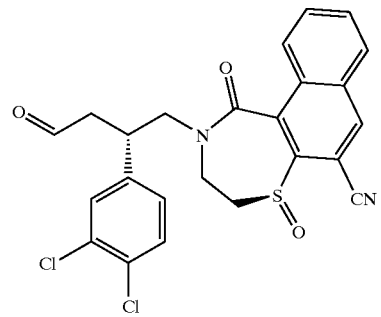

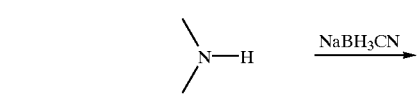

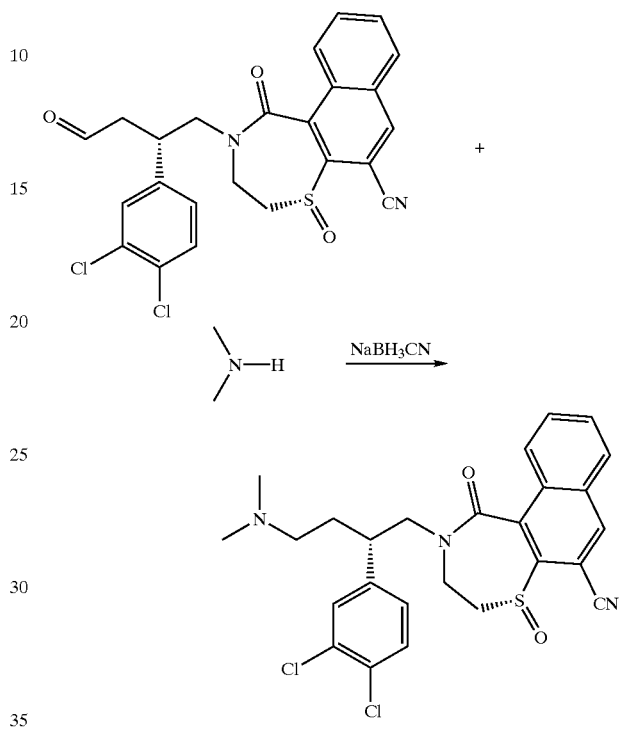

By the method described in Example 79, Intermediate 78b (19 mg, 0.04 mmol) and dimethylamine hydrochloride (5 mg, 0.06 mmol) were converted to 15 mg of the title compound.

Example 81

(5R)-2-[(2S)-2-(3,4-dichlorophenyl)-4-(dimethylamino)butyl]-1-oxo-1,2,3,4-tetrahydronaphtho[1,2-f][1,4]thiazepine-6-carbonitrile 5-oxide By the method described in Example 79, Intermediate 78c (10 mg, 0.021 mmol) and dimethylamine hydrochloride (5 mg, 0.06 mmol) were converted to 10 mg of the title compound.

Example 82

2-[(2S)-2-(3,4-dichlorophenyl)-4-(methoxyamino)butyl]-1-oxo-1,2,3,4-tetrahydronaphtho[1,2-f][1,4]thiazepine-6-carbonitrile

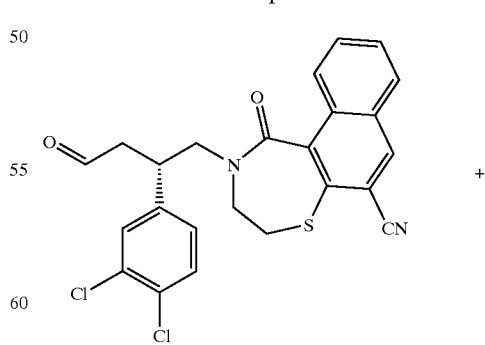

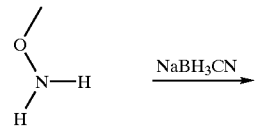

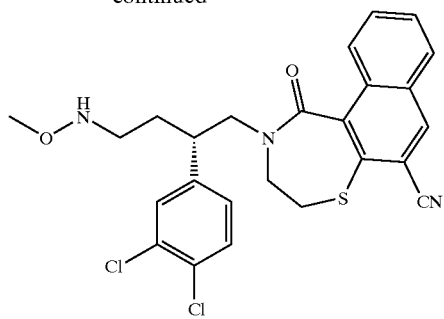

By the method described in Example 79, Intermediate 78a (40 mg, 0.085 mmol) and methoxyamine hydrochloride (13 mg, 0.154 mmol) were converted to 28 mg of the title compound.

Example 83

(5)-2-[(2S)-2-(3,4-dichlorophenyl)-4-(methoxyamino)butyl]-1-oxo-1,2,3,4-tetrahydronaphtho[1,2-f][1,4]thiazepine-6-carbonitrile 5-oxide

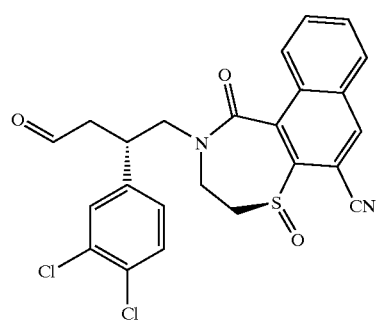

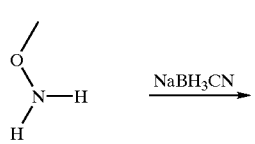

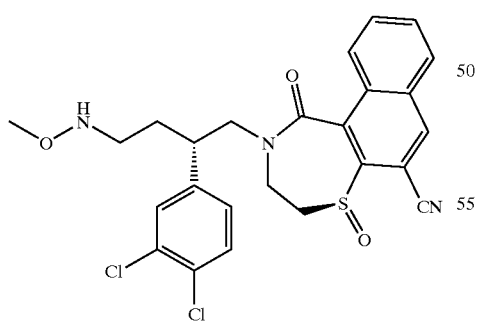

By the method described in Example 79, Intermediate 78b (30 mg, 0.06 mmol) and methoxyamine hydrochloride (5 mg, 0.06 mmol) were converted to crude product. The crude product was purified on a C-8 reverse phase column eluting with a 40–70% $CH_3CN/H_2O$ gradient (0.05% TFA) to give 15 mg of the title compound as its trifluoroacetic acid salt.

Example 84

2-[(2S)-2-(3,4-dichlorophenyl)-4-(cyclopropylamino)butyl]-1-oxo-1,2,3,4-tetrahydronaphtho[1,2-f][1,4]thiazepine-6-carbonitrile

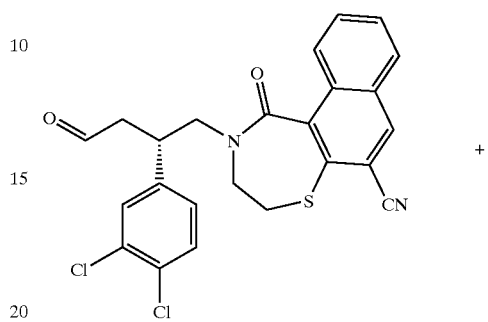

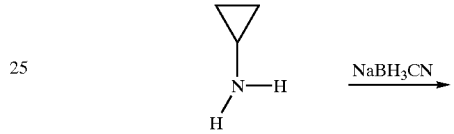

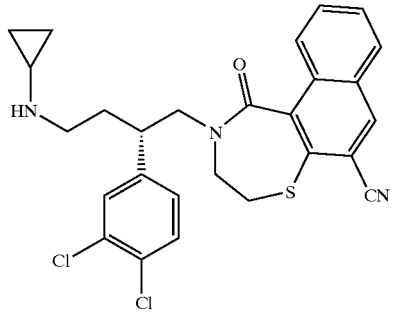

By the method described in Example 83, Intermediate 78a (70 mg, 0.15 mmol) and cyclopropylamine (13 mg, 0.23 mmol) were converted to 45 mg of the title compound as its trifluoroacetic acid salt.

| Sulfur Compound LC/MS Parameters | |
|---|---|
| Column: | HP C-8 5 cm 5 micron 2.1 mm |
| Method I: | Fast LC/MS Method |
| | 1.4 ml/min    5% B |
| | 0–3 min 5–90% B |
| | 3 to 4 min hold at 90% B |
| | 4–5 min 90–5% B |
| | A = 0.05% TFA in $H_2O$ |
| | B = 90:10 $CH_3CN:H_2O$ |
| Method II | 15 min LC/MS Method |
| | 1.4 ml/min    5% B Hold 30 sec |
| | 0.5–10 min    5–90% B |
| | 10–12 min    hold at 90% B |
| | 12–12.5 min    90–5% B |
| | 12.5–14 min    hold at 5% B |
| | A = 0.05% TFA in $H_2O$ |
| | B = 90:10 $CH_3CN:H_2O$ |

Thiazapine Final Product Retention Times

| Example | Method | Retention Time (minutes) | M + 1 | M + 3 |
|---|---|---|---|---|
| 78 | II | 8.68 | 467 | 469 |
| 79 | I | 2.25 | 498 | 500 |
| 80 | I | 1.98 | 514 | 516 |
| 81 | I | 1.96 | 514 | 516 |
| 82 | II | 6.64 | 500 | 502 |
| 83 | I | 2.12 | 516 | 518 |
| 84 | II | 6.69 | 510 | 512 |

What is claimed is:
1. A compound having the formula

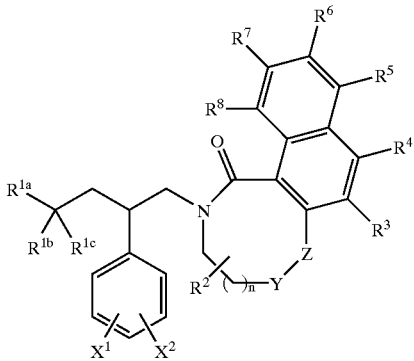

wherein:
$R^{1a}$ is H, $NR^9R^{10}$, —$OR^{10}$, Cl, Br,

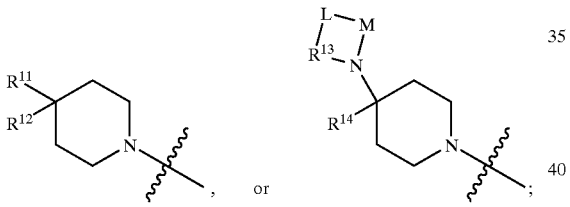

$R^{1b}$ and $R^{1c}$ are independently H or —$OR^9$, or $R^{1b}$ and $R^{1c}$ together are =O, =$CH_2$ or —$OCH_2CH_2O$—;
$R^2$ is H, oxo, —$OR^9$ or —$CH_3$;
$R^3$, $R^4$, $R^5$, $R^6$, $R^7$ and $R^8$ are each independently selected from H, cyano, nitro, trifluoromethoxy, trifluoromethyl, $C_{1-6}$alkylsulfonyl, halo, —$OR^9$, —$OCH_2O$—, $C_{1-6}$alkyl, $C_{2-6}$alkenyl, $C_{2-6}$alkynyl, —C(=O)$R^9$, —C(=O)$NR^9R^{10}$, —OC(=O)$R^9$, —$NR^9$C(=O)$R^{10}$, aminosulfonyl and $C_{1-6}$alkyl substituted by any of the hereinabove substituents; wherein at least two of $R^3$, $R^4$, $R^5$, $R^6$, $R^7$ and $R^8$ are H;
$R^9$ is independently selected From H, $C_{1-6}$alkyl, $C_{1-4}$alkoxy, and —$OCH_2(CH_2)_n$phenyl;
$R^{10}$ is independently H or $C_{1-6}$alkyl, hydroxy$C_{1-6}$alkyl, ($NR^9R^9$)$C_{1-6}$alkyl, ($NR^9R^9$)C(=O)$C_{1-6}$alkyl, —$(CH_2)_oR^{15}$;
$R^{11}$ is phenyl, substituted in at least the ortho position by $C_{1-6}$alkylthio, $C_{1-6}$alkylsulfinyl, $C_{1-6}$alkylsulfonyl, trifluoromethylthio, trifluoromethylsulfinyl, $C_{1-6}$alkanesulfonamido, $C_{1-6}$alkanoyl, $C_{1-6}$alkoxycarbonyl, succinamido, carbamoyl, $C_{1-6}$alkylcarbamoyl, di-$C_{1-6}$alkylcarbamoyl, $C_{1-6}$alkoxy-CC$_{1-6}$alkylcarbamoyl, N-methylcarbamoyl, $C_{1-6}$alkanoylamino, ureido, $C_{1-6}$ureido, di-$C_{1-6}$alkylureido, amino, $C_{1-6}$alkylamino, or di-$C_{1-6}$alkylamino;

$R^{12}$ is selected from hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl and bis($C_{1-6}$alkyl)carbamoyl;
$R^{13}$ is —$CH_2CH_2$—, $CH_2CH_2CH_2$— or —$CH_2CH_2CH_2CH_2$—;
$R^{14}$ is hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl or di-$C_{1-6}$alkylcarbamoyl;
$R^{15}$ is a 5- or 6-membered saturated or unsaturated heterocycle containing 1 or 2 heteroatoms selected from nitrogen, oxygen and sulfur and additionally susbituted with 0 or 1 oxo groups; or $R^{15}$ is phenyl substituted by 0, 1, or 2 substituents selected from halogen, $C_{1-4}$alkoxy, vicinal-methylenedioxy, —S(=O)$_n$$C_{1-4}$alkyl, —S(=O)$_2$$NH_2$ and $C_{1-4}$alkyl;
M is —C(=O)— or —S(=O)$_2$—;
L is —NH— or —$CH_2$—;
$X^1$ and $X^2$ are independently H or halogen, wherein at least one of $X^1$ and $X^2$ are halogen;
Y and Z are independently selected from $CH_2$, O, S, S=O and S(=O)$_2$, wherein at least one of Y and Z is $CH_2$;
n is independently, at each instance, 0 or 1;
o is independently, at each instance, 1, 2 or 3; and
any pharmaceutically-acceptable salt thereof.
2. A compound according to claim 1, wherein:
$R^5$, $R^6$, $R^7$ and $R^8$ are each H.
3. A compound according to claim 2, wherein:
$R^{1a}$ is H, $NR^9R^{10}$, —$OR^{10}$, Cl or Br;
$R_{1b}$ and $R^{1c}$ are independently H or —$OR^9$, or $R^{1b}$ and $R^{1c}$ together are =O, =$CH_2$ or —$OCH_2CH_2O$—.
4. A compound according to claim 2, wherein:
$R^{1a}$ is Cl or Br, and
$R^{1b}$ and $R^{1c}$ are both H.
5. A compound according to claim 2, wherein:
$R^{1a}$ is $NR^9R^{10}$, —$OR^{10}$; and
$R^{1b}$ and $R^{1c}$ are both H or $R^{1b}$ and $R^{1c}$ together are =O.
6. A compound according to claim 1, wherein
$R^{1a}$ is H, $NR^9R^{10}$, —$OR^9$,

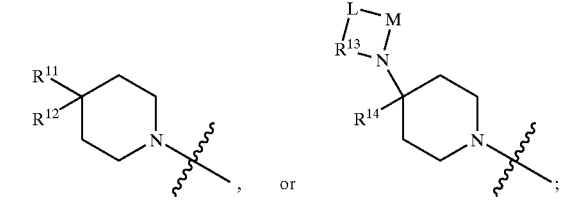

$R^{1b}$ and $R^{1c}$ are independently H or —$OR^9$, or $R^{1b}$ and $R^{1c}$ together are =O, =$Ch_2$ or —$OCH_2CH_2O$—;
$R^2$ is H, oxo, —$OR^9$ or —$CH^3$;
$R^3$, $R^4$, $R^5$, $R^6$, $R^7$ and $R^8$ are each independently selected from H, cyano, nitro, trifluoromethoxy, trifluoromethyl, $C_{1-6}$alkylsulfonyl, halo, —$OR^9$, —$OCH_2O$—, $C_{1-6}$alkyl, $C_{2-6}$alkonyl, $C_{2-6}$alkynyl, —C(=O)$R^9$, —C(=O)$NR^9R^{10}$, —OC(=O)$R^9$, —$NR^9$C(=O)$R^{10}$, aminosulfonyl and $C_{1-6}$alkyl substituted by any of the hereinabove substituents; wherein at least two or $R^3$, $R^4$, $R^5$, $R^6$, $R^7$ and $R^8$ are H;

$R^9$ and $R^{10}$ are each independently H or $C_{1-6}$alkyl;

$R^{11}$ is phonyl, substituted in at least the ortho position by $C_{1-6}$alkylthio, $C_{1-6}$alkylsulfinyl, $C_{1-6}$alkylsulfonyl, trifluoromethylthio, trifluoromethylsulfinyl, $C_{1-6}$alkanesulfonamido, $C_{1-6}$alkanoyl, $C_{1-6}$alkoxycarbonyl, succinamido, carbamoyl, $C_{1-6}$alkylcarbamoyl, di-$C_{1-6}$alkylcarbamoyl, $C_{1-6}$alkoxy-$C_{1-6}$alkylcarbamoyl, N-methylcarbamoyl, $C_{1-6}$alkanoyamino, ureido, $C_{1-6}$ureido, di-$C_{1-6}$alkylureido, amino, $C_{1-6}$alkylamino, or di-$C_{1-6}$alkylamino;

$R^{12}$ is selected from hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl and bis($C_{1-6}$alkyl)carbamoyl;

$R^{13}$ is —$CH_2CH_2$—, —$CH_2CH_2CH_2$— or —$CH_2CH_2CH_2CH_2$—;

$R^{14}$ is hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl or di-$C_{1-6}$alkylcarbamoyl;

M is —C(=O)—0 or

L is —NH— or —$CH_2$—;

$X^1$ and $X^2$ are independently H or halogen, wherein at least one of $X^1$ and $X^2$ are halogen;

Y and Z are $CH_2$ or O, wherein Y does not equal Z;

n is 0 or 1; and any pharmaceutically-acceptable salt thereof.

7. A compound according to claim 6 wherein $R^3$, $R^4$, $R^5$, $R^6$, $R^7$ and $R^8$ are selected from H, cyano, nitro, —S(=O)$C_{1-6}$alkyl, halo, —$OR^9$, —$OCH_2O$—, $C_{1-6}$alkyl, $C_{2-6}$alkenyl, $C_{2-6}$alkynyl, —C(=O)$OR^9$, —C(=O)$NR^9R^{10}$, —OC(=O)$R^9$, —$NR^9C$(=O)$R^{10}$, aminosulfonyl and —$C_{1-6}$alkylcyano; wherein at least three of $R^3$, $R^4$, $R^5$, $R^6$, $R^7$ and $R^8$ are H.

8. A compound according to claim 6 wherein $R^3$, $R^4$, $R^5$, $R^6$, $R^7$ and $R^8$ are selected from H, cyano, methoxy, ethoxy, isopropoxy, fluoro, fluoro, chloro, iodo, nitro, cyanomethyl, carboxy, carbamoyl, ethynyl, methyl, ethyl, dimethylcarbamoyl, methylsulfonyl, aminosulfonyl, prop-2-enyl, acetyl and acetylamino; wherein at least three of $R^3$, $R^4$, $R^5$, $R^6$, $R^7$ and $R^8$ are H.

9. A compound according to claim 6 wherein $R^3$, $R^4$, $R^5$, $R^6$, $R^7$ and $R^8$ are selected from H, cyano, methoxy, ethyl, fluoro and nitro; wherein at least three of $R^3$, $R^4$, $R^5$, $R^6$, $R^7$ and $R^8$ are H.

10. A compound according to claim 6 wherein:

$R^{1a}$ is

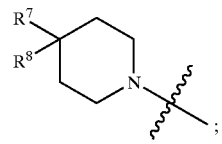

;

$R^{1b}$ is H; and $R^{1c}$ is H.

11. A compound according to claim 6, wherein:

$R^{1a}$ is

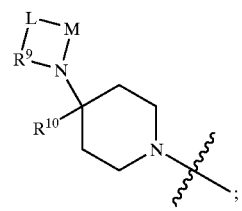

;

$R^{1b}$ is H; and $R^{1c}$ is H.

12. A compound according to claim 6, wherein $R^{1a}$ is H, $NR^9R^{10}$ or —$OR^9$.

13. A compound according to claim 6, wherein $R^2$ is —$OR^5$ or —$CH_3$.

14. A pharmaceutical composition comprising a therapeutically-effective amount of a compound according to claim 1.

15. A method of treating major depressive disorder or comprising administering a therapeutically-effective amount of an NK1 antagonist according claim 1.

* * * * *